(12) United States Patent
Tsai et al.

(10) Patent No.: US 12,336,960 B2
(45) Date of Patent: Jun. 24, 2025

(54) CLOSED SYSTEM TRANSFER DEVICE

(71) Applicant: ADVCARE MEDICAL, INC., New Taipei (TW)

(72) Inventors: Hsi-chin Tsai, New Taipei (TW); Jhih-Syuan Jhou, New Taipei (TW)

(73) Assignee: ADVCARE MEDICAL, INC., New Taipei (TW)

( * ) Notice: Subject to any disclaimer, the term of this patent is extended or adjusted under 35 U.S.C. 154(b) by 432 days.

(21) Appl. No.: 18/011,027

(22) PCT Filed: Jun. 17, 2020

(86) PCT No.: PCT/CN2020/096512
§ 371 (c)(1),
(2) Date: Dec. 16, 2022

(87) PCT Pub. No.: WO2021/253264
PCT Pub. Date: Dec. 23, 2021

(65) Prior Publication Data
US 2023/0240939 A1 Aug. 3, 2023

(51) Int. Cl.
*A61J 1/14* (2023.01)
*A61M 5/31* (2006.01)

(52) U.S. Cl.
CPC .............. *A61J 1/14* (2013.01); *A61M 5/3129* (2013.01)

(58) Field of Classification Search
CPC .... A61J 1/14; A61J 1/201; A61M 2005/3114; A61M 5/1782; A61M 5/19;
(Continued)

(56) References Cited

U.S. PATENT DOCUMENTS 3,896,805 A * 7/1975 Weingarten ............. A61M 5/32
604/203
8,172,795 B2 5/2012 Lum et al.
(Continued)

FOREIGN PATENT DOCUMENTS

CN 1583187 A 2/2005
CN 105722493 A 6/2016

OTHER PUBLICATIONS

International Search Report for International Application No. PCT/CN2020/096512, dated Mar. 5, 2021, with an English translation.

*Primary Examiner* — Kai H Weng
(74) *Attorney, Agent, or Firm* — Birch, Stewart, Kolasch & Birch, LLP

(57) ABSTRACT

A closed system transfer device (CSTD) includes a barrel, a plunger, and a connecting port fixed to the barrel. The barrel includes a first cavity and a second cavity, which are separated. A piston of the plunger is operably moved within the first cavity and divides the first cavity into a first region and a second region that communicates with the second cavity. The connecting port includes a first channel communicating with the first cavity and a second channel communicating with the second cavity. When the CSTD is connected to a drug-liquid container to draw liquid, the first region is enlarged to draw the liquid into the first region from the container through the first channel. Simultaneously, the second region is reduced to discharge air in the second region to the container through the second cavity and the second channel. Thus, the CSTD and the container form a closed environment.

26 Claims, 34 Drawing Sheets

(58) Field of Classification Search
CPC .............. A61M 5/3129; A61M 5/3134; A61M 5/3135; A61M 5/3293; A61M 5/3295; A61M 5/344
See application file for complete search history.

(56) References Cited

U.S. PATENT DOCUMENTS

| | | | |
|---|---|---|---|
| 2004/0064102 A1* | 4/2004 | Yamada | A61M 5/19 604/191 |
| 2012/0283596 A1 | 11/2012 | Seiger et al. | |
| 2016/0129192 A1* | 5/2016 | Rothenberg | A61M 5/3135 604/506 |

* cited by examiner

CLOSED SYSTEM TRANSFER DEVICE

BACKGROUND OF THE INVENTION

Technical Field

The present invention relates generally to a medical transfer device, and more particularly to a closed system transfer device that constitutes a closed environment.

Description of Related Art

A conventional medical transfer device is usually a syringe with a needle. The needle of the syringe could be pierced through the drug liquid container to draw a drug liquid into the syringe, and then be injected into a patient. After that, the medical staff covers the needle by using a protective cover and removes the needle from the syringe. However, in practice, the medical staff has a high risk of being pierced by the needle, because of giving too many injections or being out of practice. Thus, the risk of being infected is significantly increased.

When the drug liquid is volatile, the conventional medical transfer device may cause a concentration error due to an improper operation, leading to a significant danger. Besides, inhaling the volatile drug liquid is probably harmful to humans. In case, the medical staff carelessly inhales too much volatile drug liquid during drug liquid preparation, it could be harmful to the health of the medical staff.

On the other hand, some kinds of drug liquid could provide a specific function by mixing right before injection. These kinds of drug liquid are prepared by mixing a first liquid and a second liquid according to a certain ratio. Based on the using method of the conventional medical transfer device, the needle is pierced into a container having the first liquid to draw the first liquid into the syringe, and then the same needle is pierced into another container having the second liquid to draw the second liquid into the syringe. As a result, the first liquid and the second liquid could be mixed within the syringe and prepared ready for injection to the patient. In such a situation, when the needle is inserted into the second liquid, the first liquid that remains on the needle may contaminate the second liquid in the container. By repeating the preparation process, the concentration and content of the liquid in the container of the second liquid become inaccurate and impure, which can not be used anymore, leading to a waste of the drug liquid.

To sum up, a novel medical transfer device is needed for solving the problem of the conventional medical transfer device.

BRIEF SUMMARY OF THE INVENTION

In view of the above, the primary objective of the present invention is to provide a closed system transfer device, wherein the closed system transfer device does not include a needle that is exposed outside, so that a problem that a medical staff is hurt by the needle during an operation could be prevented, thereby reducing a risk of being infected during a medical process. Additionally, the closed system transfer device provided by the present invention and a drug liquid container could jointly create a closed environment, so that a concentration error caused by volatilization of the volatile drug liquid during the operation could be avoided. Additionally, with such design, the medical staff could avoid inhaling the volatile drug liquid, thereby reducing a possible health threat to the medical staff. Furthermore, the closed system transfer device provided by the present invention could avoid using the same needle to draw different liquids, so that contamination between different kinds of drug liquid could be prevented, thereby reducing the waste of the medical liquid.

The present inventive subject matter provides a closed system transfer device, including a barrel, a plunger, and a connecting port. The barrel includes a tube wall and an isolating wall, wherein the tube wall encircles to form a receiving space, and the isolating wall is disposed in the receiving space to form a first cavity and a second cavity, which are separated from each other. The plunger includes a sealing cap, a rod body, an operating member, and a piston, wherein the sealing cap is fixed to and seals a first end opening of the barrel, and the rod body passes through a perforation of the sealing cap; an end of the rod body is connected to the operating member, and another end of the rod body is connected to the piston. The piston is airtightly disposed in the first cavity of the barrel and is controllable to move within the first cavity; the piston divides the first cavity into a first region and a second region, wherein the second region is closer to the first end opening of the barrel than the first region; the first region does not communicate with the second region within the barrel; the second region communicates with the second cavity at the first end opening. The connecting port is fixed to a second end opening of the barrel, wherein the second end opening is opposite to the first end opening. The connecting port includes a first channel, a second channel, and at least one soft plug. The first channel communicates with the first cavity, and the second channel communicates with the second cavity. The at least one soft plug is airtightly fixed to an end of the first channel and an end of the second channel to create a closed environment of the closed system transfer device. When the closed system transfer device is connected to a drug liquid container, the at least one soft plug is operable to be broken to allow the first channel to communicate with the second channel via the drug liquid container. When the operating member of the plunger is pulled by an external force, the rod body drives the piston to move in a direction toward the first end opening of the barrel. The first region of the first cavity is enlarged to draw a drug liquid in the drug liquid container into the first region through the first channel. Simultaneously, the second region is reduced, and air in the second region is discharged to the drug liquid container through the second cavity and the second channel, so that the closed system transfer device and the drug liquid container form another closed environment.

With such design, the closed system transfer device does not include a needle that is exposed outside, so that the medical staff could not be pierced by the needle, thereby reducing the risk of being infected during the operation of the closed system transfer device. Additionally, the closed system transfer device of the present invention and the drug liquid container could jointly form a closed environment, so that the concentration error due to the volatilization of the drug liquid could be avoided. Moreover, the medical staff could be protected from inhaling the volatile drug liquid that is harmful to the health. Furthermore, the closed system transfer device of the present invention could avoid using a single needle to draw different kinds of drug liquid, so that the different kinds of drug liquid could be free of being contaminated, thereby reducing the waste of the drug liquid.

BRIEF DESCRIPTION OF THE SEVERAL VIEWS OF THE DRAWINGS

The present invention will be best understood by referring to the following detailed description of some illustrative embodiments in conjunction with the accompanying drawings, in which

FIG. 17-1 is an enlarged partial view of the operating member and the sealing cap in FIG. 15;

FIG. 17-2 is similar to FIG. 17-1, showing the operating member and the sealing cap of another embodiment;

DETAILED DESCRIPTION OF THE INVENTION

As illustrated in FIG. 1 to FIG. 10, a closed system transfer device 10 of a first embodiment according to the present invention includes a barrel 12, a plunger 14, and a connecting port 16.

Figure 4:
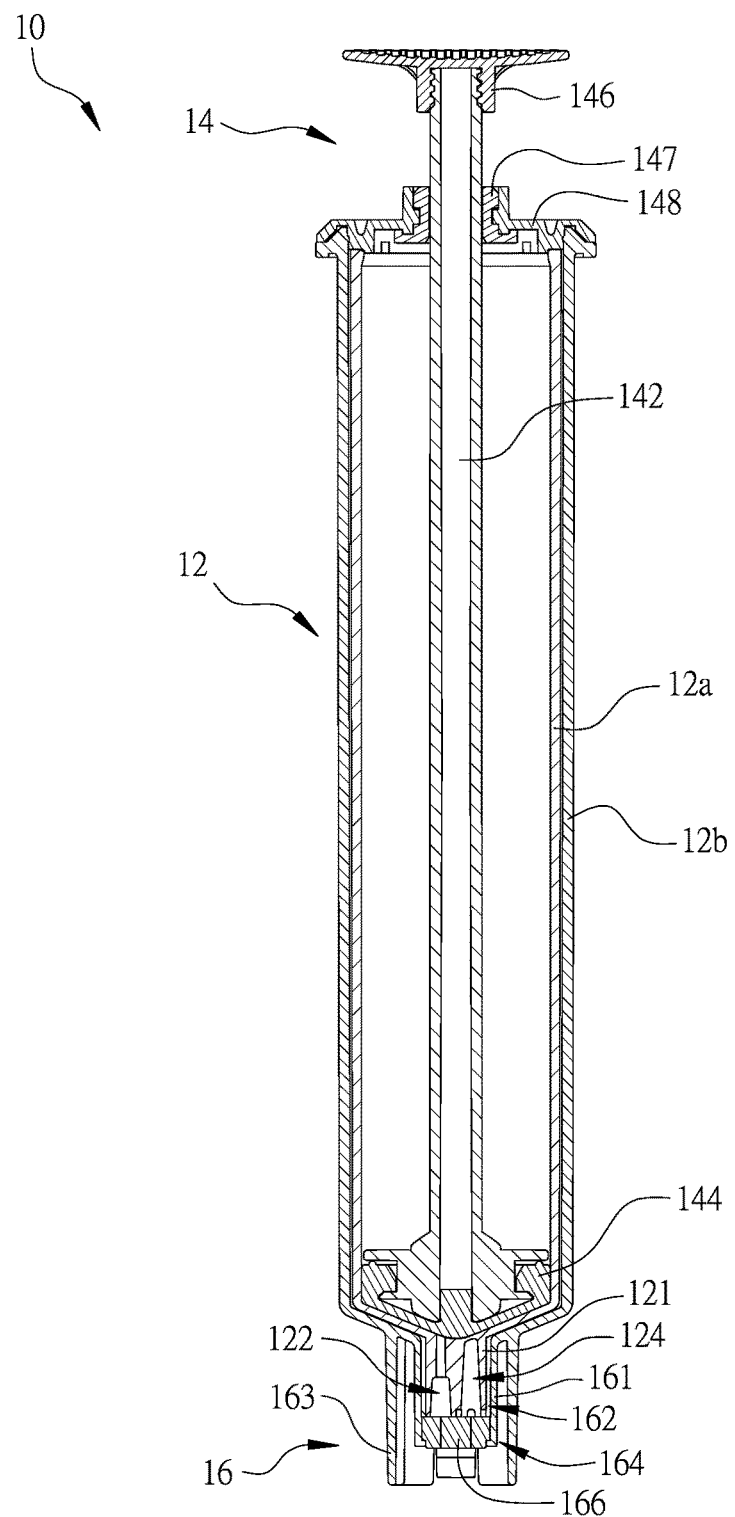
FIG. 4 is a section view taken along the 4-4 line in FIG. 3.

The barrel 12 includes a tube wall and an isolating wall, wherein the tube wall encircles to form a receiving space, and the isolating wall is disposed in the receiving space to form a first cavity and a second cavity, which are separated from each other. In the first embodiment, the tube wall of the barrel 12 is a first tube body 12b that has the receiving space, and the isolating wall encircles to form a second tube body 12a, and the second tube body 12a is disposed in the receiving space of the first tube body 12b. A space encircled by the second tube body 12a constitutes the first cavity of the barrel 12, and a space formed between the first tube body 12b and the second tube body 12a constitutes the second cavity 162 of the barrel 12, as shown in FIG. 4.

Figure 8:
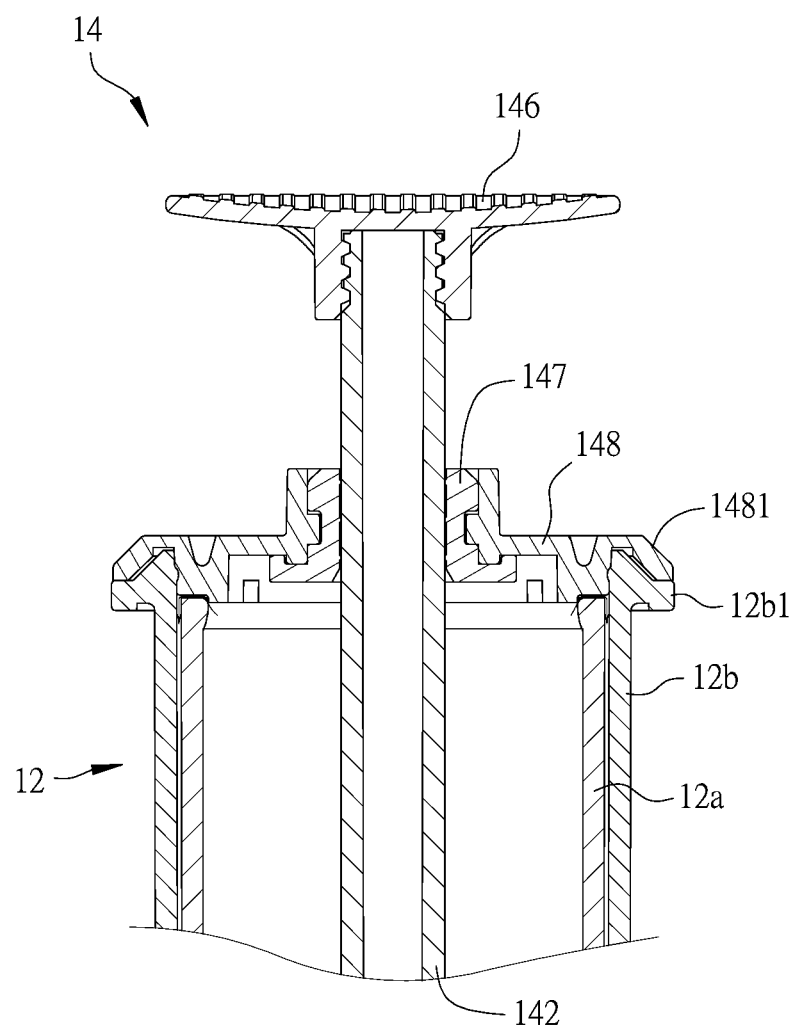
FIG. 8 is an enlarged partial view of the operating member and the sealing cap in FIG. 4.
Figure 9:
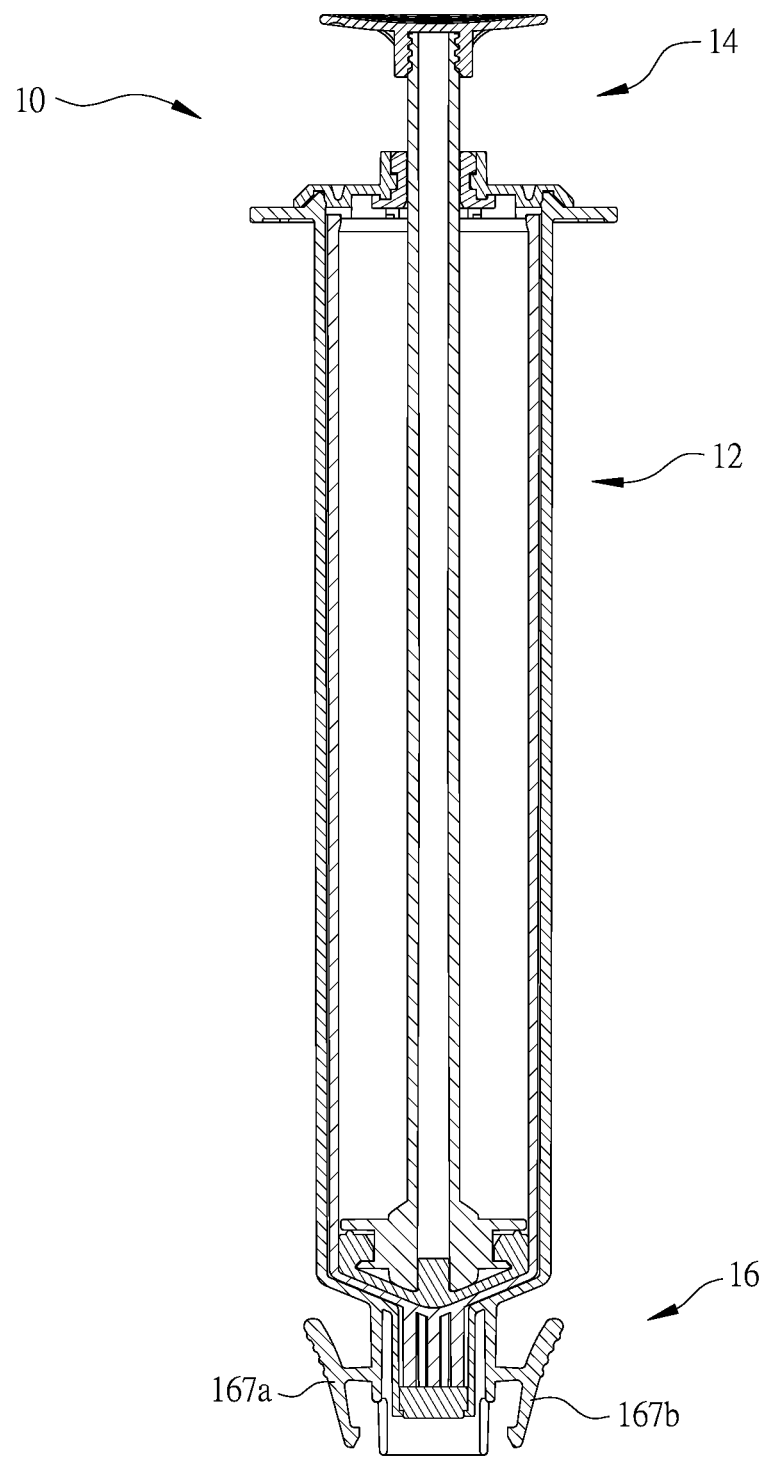
FIG. 9 is a section view taken along the 9-9 line in FIG. 3.

The plunger 14 includes a rod body 142, a piston 144, an operating member 146, and a sealing cap 148, wherein the sealing cap 148 is fixed to and seals a first end opening of the barrel 12. In the first embodiment, a connecting portion 1481 of the sealing cap 148 is tightly connected to a connected portion 12b1 of the first tube body 12b, wherein a means of connecting the connecting portion 1481 of the sealing cap 148 and the connected portion 12b1 of the first tube body 12b includes adhering and high-frequency welding. The rod body 142 passes through a perforation of the sealing cap 148. An end of the rod body 142 is connected to the operating member 146, and another end of the rod body 142 is connected to the piston 144. In the first embodiment, the plunger 14 includes a sealing ring 147 that fits around the rod body 142 and is located at the perforation of the sealing cap 148, as shown in FIG. 8. The piston 144 is airtightly disposed in the first cavity of the barrel 12 and is controllable to move within the first cavity. The piston 144 divides the first cavity into a first region and a second region, wherein the second region is closer to the first end opening of the barrel 12 than the first region. The first region does not communicate with the second region within the barrel 12. The second region communicates with the second cavity at the first end opening. In the first embodiment, the first tube body 12b has the first end opening, and the sealing cap is fixed to the first end opening of the first tube body 12b to seal the first end opening, but the sealing cap does not seal the second tube body 12a to allow the second region of the first cavity to communicate with the second cavity 162 at the first end opening.

The connecting port 16, 16' is fixed to a second end opening of the barrel 12, 12', wherein the second end opening is opposite to the first end opening. The connecting port 16, 16' includes a first channel 122, a second channel 124, and at least one soft plug 166. The first channel 122 communicates with the first cavity, and the second channel 124 communicates with the second cavity 162. The soft plug 166 is airtightly fixed to an end of the first channel 122 and an end of the second channel 124 to create a closed environment of the closed system transfer device 10.

When the closed system transfer device 10 is connected to a drug liquid container (not shown), the soft plug 166 could be operated to break. After the soft plug 166 is broken, the first channel 122 communicates with the second channel 124 via the drug liquid container. When the operating member 146 of the plunger 14 is pulled by an external force, the rod body 142 drives the piston 144 to move in a direction toward the first end opening of the barrel 12, so that the first region of the first cavity is enlarged to draw a drug liquid in the drug liquid container into the first region through the first channel 122. Simultaneously, the second region is reduced, and air in the second region is discharged to the drug liquid container through the second cavity 162 and the second channel 124. Thus, the closed system transfer device 10 and the drug liquid container form another closed environment.

Figure 5:
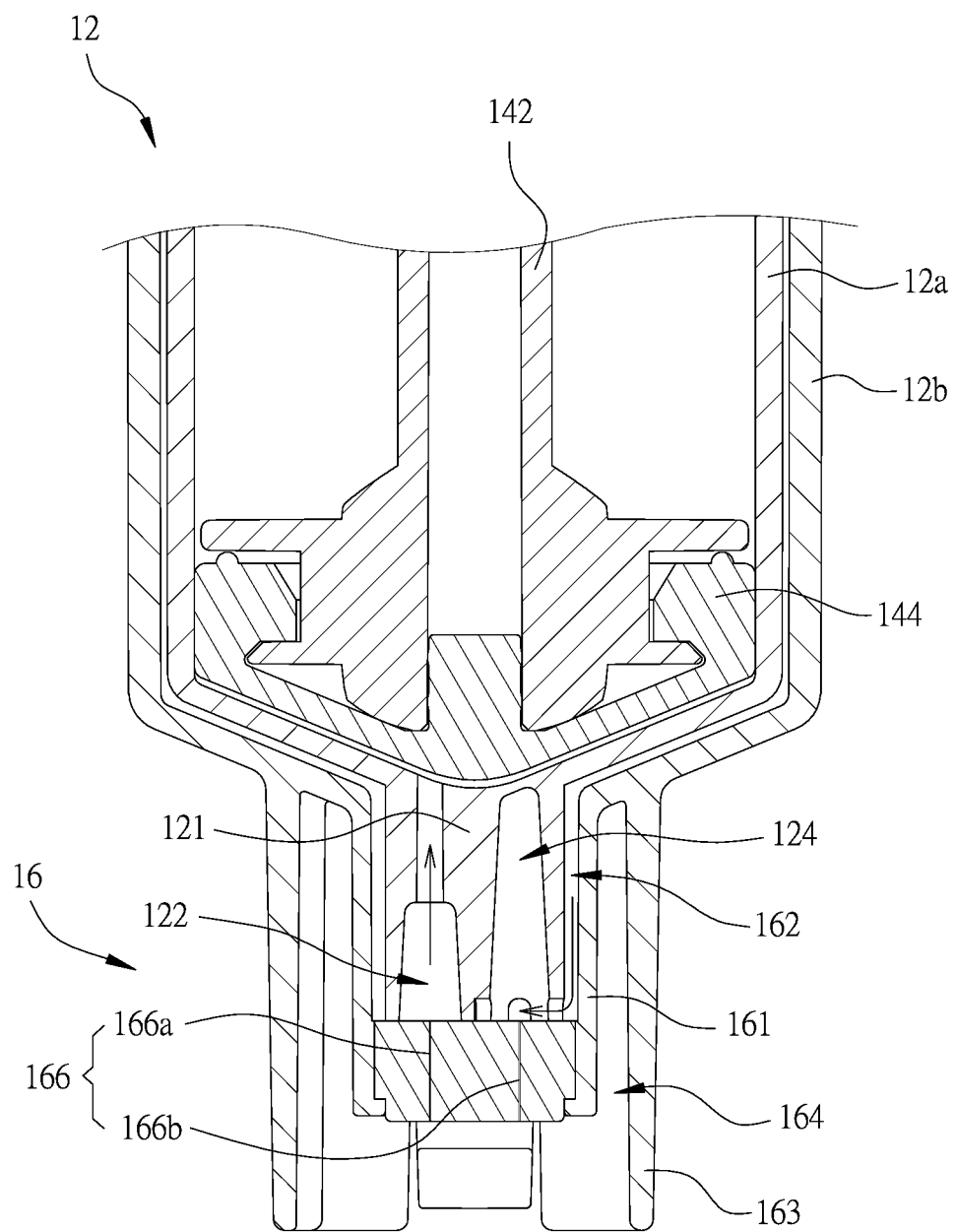
FIG. 5 is an enlarged partial view of the connecting port in FIG. 4.

In the first embodiment, the connecting port 16 includes at least one protruding column 121, wherein the protruding column 121 is fixed to the second end opening of the barrel 12. The first channel 122 and the second channel 124 are disposed in the protruding column 121. The soft plug 166 is airtightly fixed to an end of the protruding column 121, which is away from the barrel 12, as shown in FIG. 5. As illustrated in FIG. 5, the soft plug 166 has two pin holes 166a, 166b, wherein one of the two pin holes 166a communicates with the first channel 122, and the other one of the two pin holes 166b communicates with the second channel 124.

The protruding column 121 is fixed to the second tube body 12a of the barrel 12, wherein the first channel 122 of the protruding column 12 corresponds to and communicates with the first cavity. The connecting port 16 includes at least one sleeve body 161 that receives the protruding column 121. In other words, the at least one sleeve body 161 surrounds the protruding column 121. The soft plug 166 is airtightly clamped between the protruding column 121 and the sleeve body 161.

In the first embodiment, the protruding column 121 has a first side and a second side, which face opposite directions, wherein the first channel 122 is closer to the first side than the second side, and the second channel 124 is closer to the second side than the first side. The sleeve body 161 has a first wall and a second wall, which face opposite directions, wherein the first side of the protruding column 121 corresponds to the first wall of the sleeve body 161, and the second side of the protruding column 121 corresponds to the second wall of the sleeve body 161. Since an outer diameter of the first side is different from an outer diameter of the second side of the sleeve body 161, and an inner diameter of the first wall is different from an inner diameter of the second wall, the first side of the protruding column 121 could not be arranged to correspond to the second wall of the sleeve body 161, and the second side of the protruding column 121 could not be arranged to correspond to the first wall of the sleeve body 161.

Figure 6:
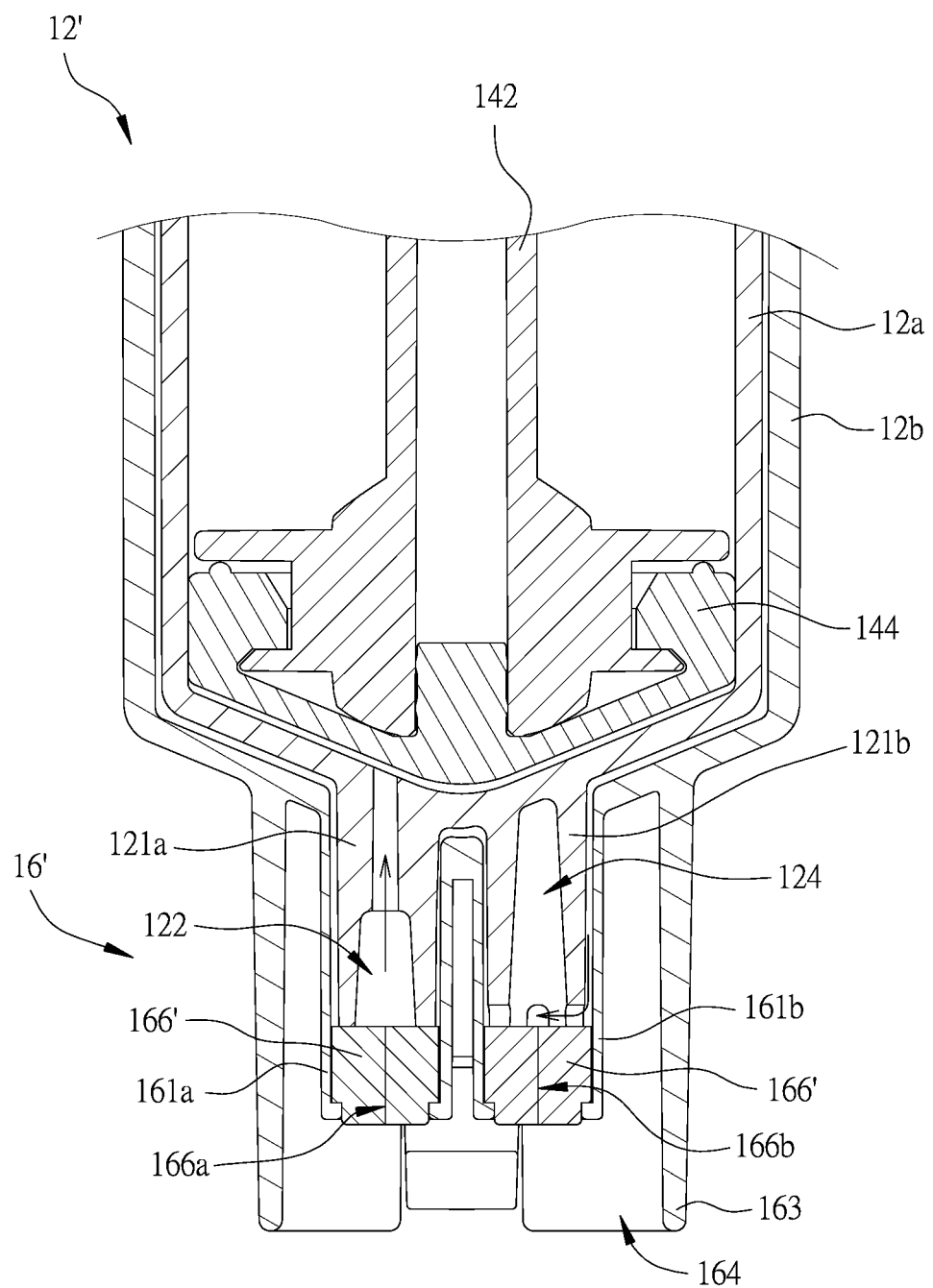
FIG. 6 is similar to FIG. 5, showing the connecting port of a second embodiment of the present invention.

A closed system transfer device of a second embodiment according to the present invention has almost the same structure as that of the first embodiment, except for the protruding column, the soft plug, and the sleeve body of the connecting port. As illustrated in FIG. 6, the protruding column of a connecting port 16' of the second embodiment includes a first protruding column 121a and a second protruding column 121b. The first channel 122 is disposed in the first protruding column 121a, and the second channel 124 is disposed in the second protruding column 121b. A soft plug 166' of the second embodiment is airtightly fixed to an end of the first protruding column 121a and an end of the second protruding column 121b, which are away from the barrel 12'. The soft plug 166' of the connecting port 16' includes a first soft plug and a second soft plug. The first soft plug is airtightly fixed to an end of the first protruding column 121a, which is away from a barrel 12'. The second soft plug is airtightly fixed to an end of the second protruding column 121b, which is away from the barrel 12'. The first protruding column 121a and the second protruding column 121b are fixed to the second end opening of the second tube body 12a of the barrel 12'. The first channel 122 in the first protruding column 121a corresponds to and communicates with the first cavity of the barrel 12'. In an embodiment, the connecting port 16' includes the sleeve body 161 that receives the first protruding column 121a and the second protruding column 121b. In other words, the at least one sleeve body 161 surrounds the first protruding column 121a and the second protruding column 121b. The soft plug 166' is airtightly clamped between the first protruding column 121a, the second protruding column 121b, and the sleeve body 161. The sleeve body 161 has the first wall and the second wall, which face opposite directions, the first protruding column 121a corresponds to the first wall of the sleeve body 161, and the second protruding column 121b corresponds to the second wall of the sleeve body 161. Furthermore, an outer diameter of the first protruding column 121a is different from an outer diameter of the second protruding column 121b, and the inner diameter of the first wall is different from the inner diameter of the second wall of the sleeve body 161. As a result, the first protruding column 121a could not be arranged to correspond to the second wall of the sleeve body 161, and the second protruding column 121b could not be arranged to correspond to the first wall of the sleeve body 161.

In the second embodiment, the at least one sleeve body includes a first sleeve body 161a and a second sleeve body 161b, and the soft plug 166' includes a first soft plug and a second soft plug. The first sleeve body 161a receives and surrounds the first protruding column 121a, and the first soft plug is airtightly clamped between the first protruding column 121a and the first sleeve body 161a. The second sleeve body 161b receives and surrounds the second protruding column 121b, and the second soft plug is airtightly clamped between the second protruding column 121b and the second sleeve body 161b, as shown in FIG. 6. Additionally, the outer diameter of the first protruding column 121a is different from the outer diameter of the second protruding column 121b, and an inner diameter of the first sleeve body 161a is different from an inner diameter of the second sleeve body 161b. As a result, the first protruding column 121a could not be disposed in the second sleeve body 161b, and the second protruding column 121b could not be disposed in the first sleeve body 161a.

As illustrated in FIG. 11 to FIG. 17, a closed system transfer device 30 of a third embodiment according to the present invention includes a barrel 32, a plunger 34, and a connecting port 36.

Figure 15:
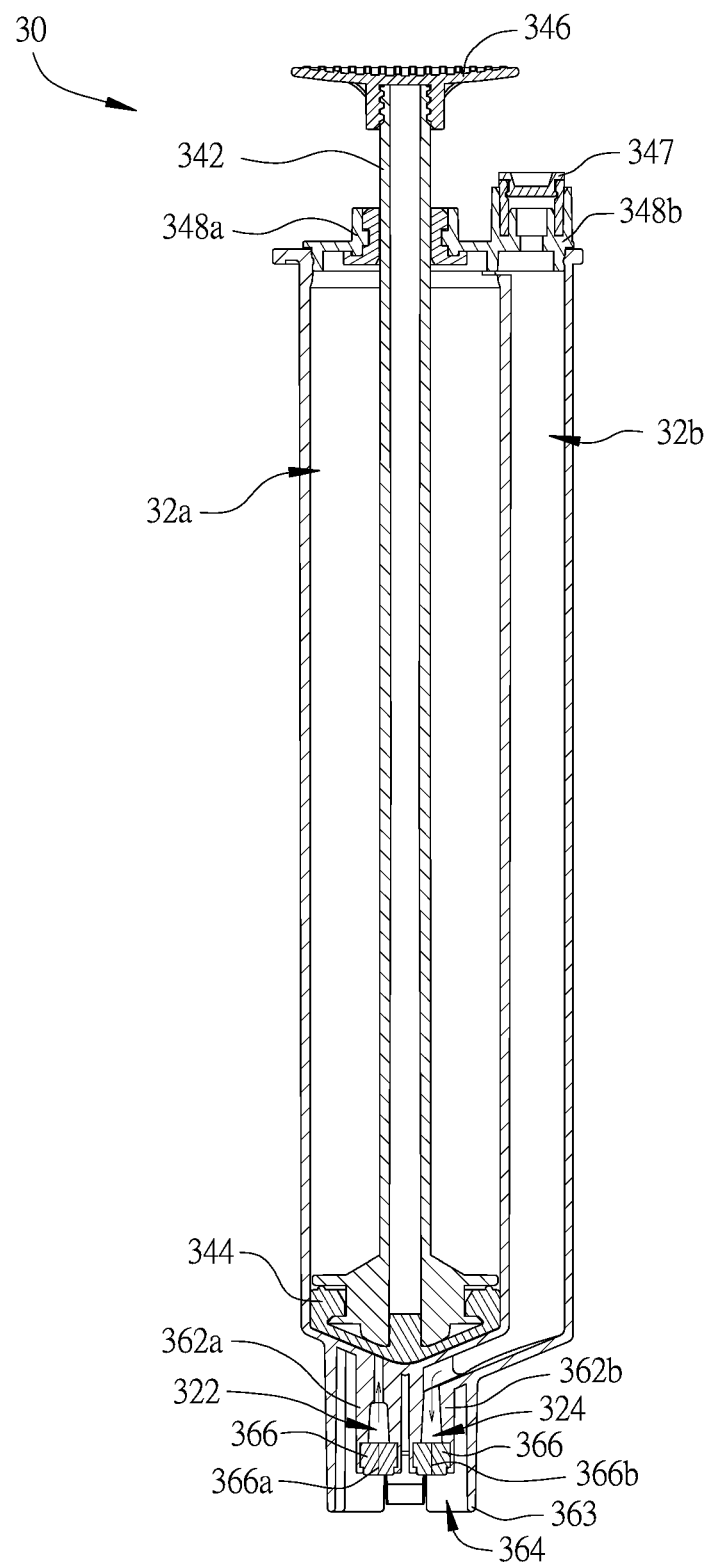
FIG. 15 is a section view taken along the 15-15 line in FIG. 14.
Figure 16:
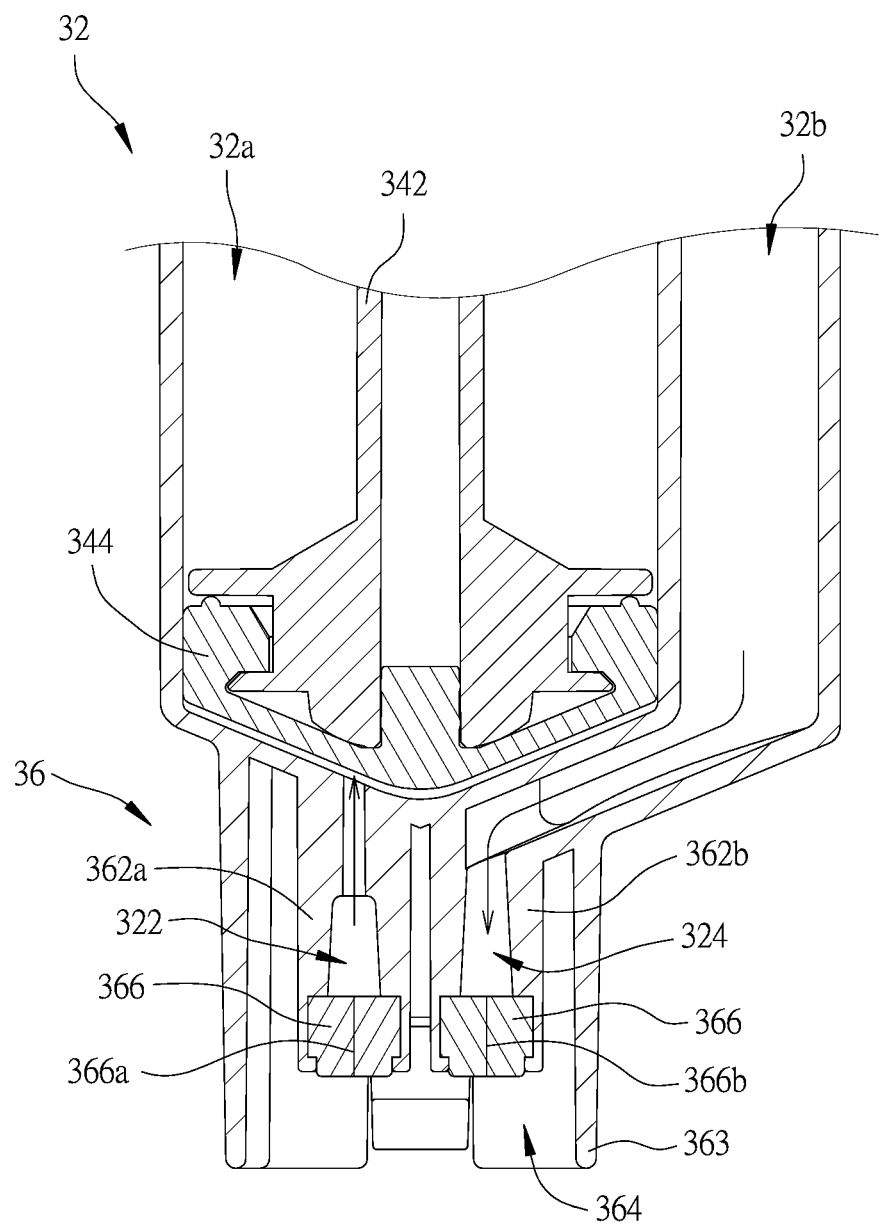
FIG. 16 is an enlarged partial view of the connecting port in FIG. 15.

As illustrated in FIG. 15, the barrel 32 is a tube body and includes a tube wall and an isolating wall, wherein the tube wall encircles to form a receiving space, and the isolating wall is disposed in the receiving space. The isolating wall is plate-shaped and is fixed to an inner side of the tube wall to divide the receiving space into a first cavity 32a and a second cavity 32b.

Figure 1:
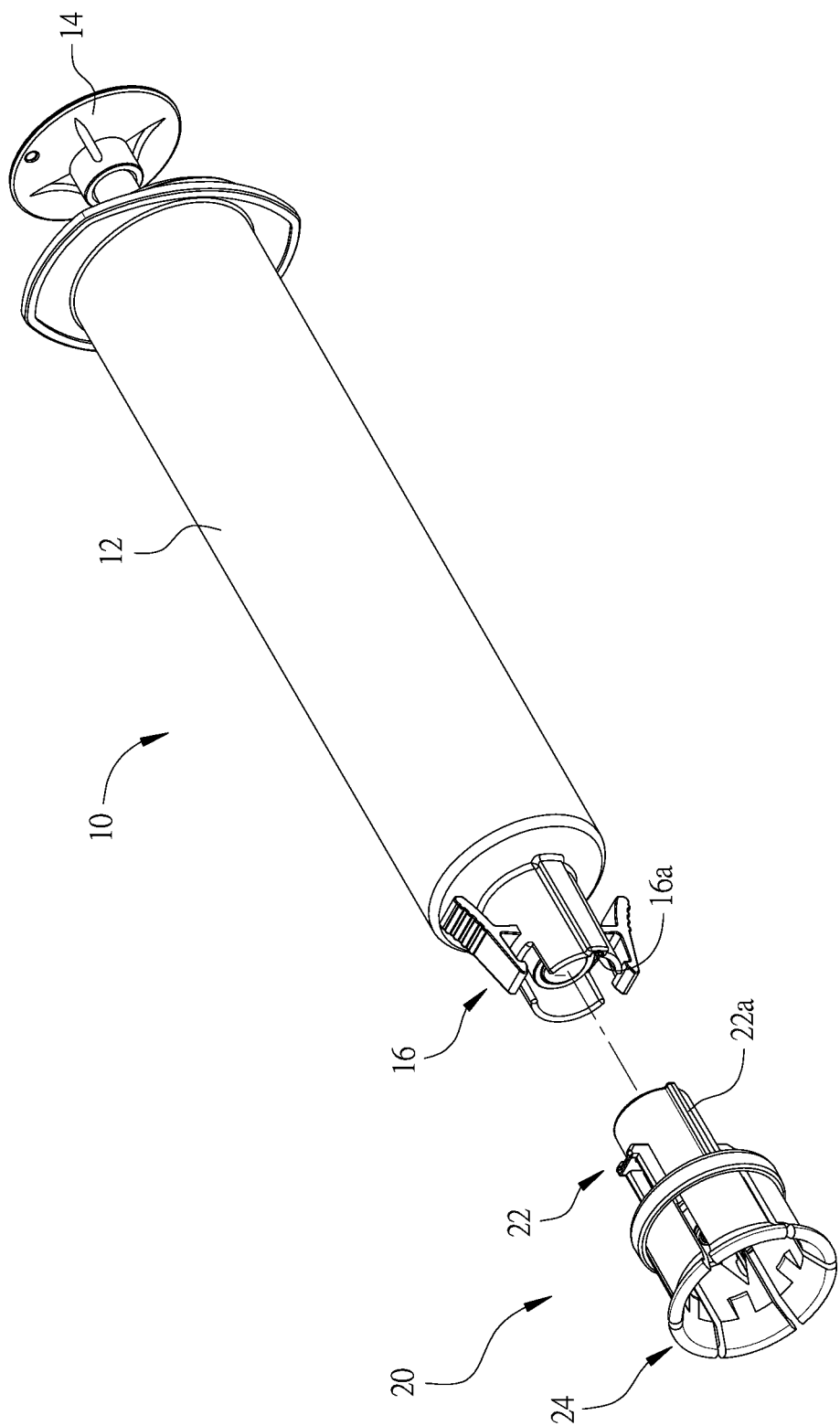
FIG. 1 is a perspective view of the closed system transfer device of a first embodiment according to the present invention.
Figures 1, 17:
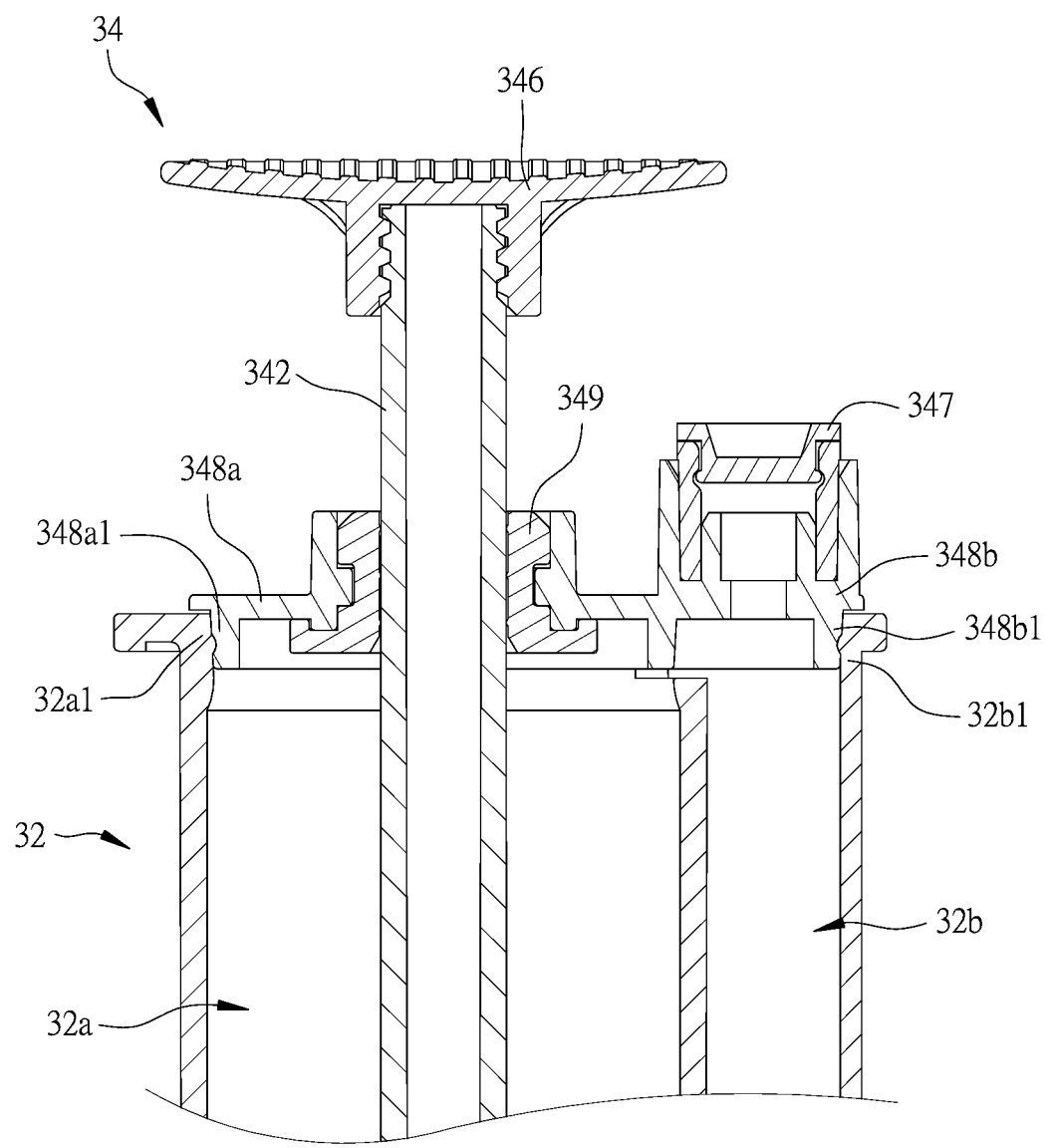
Figures 2, 17:
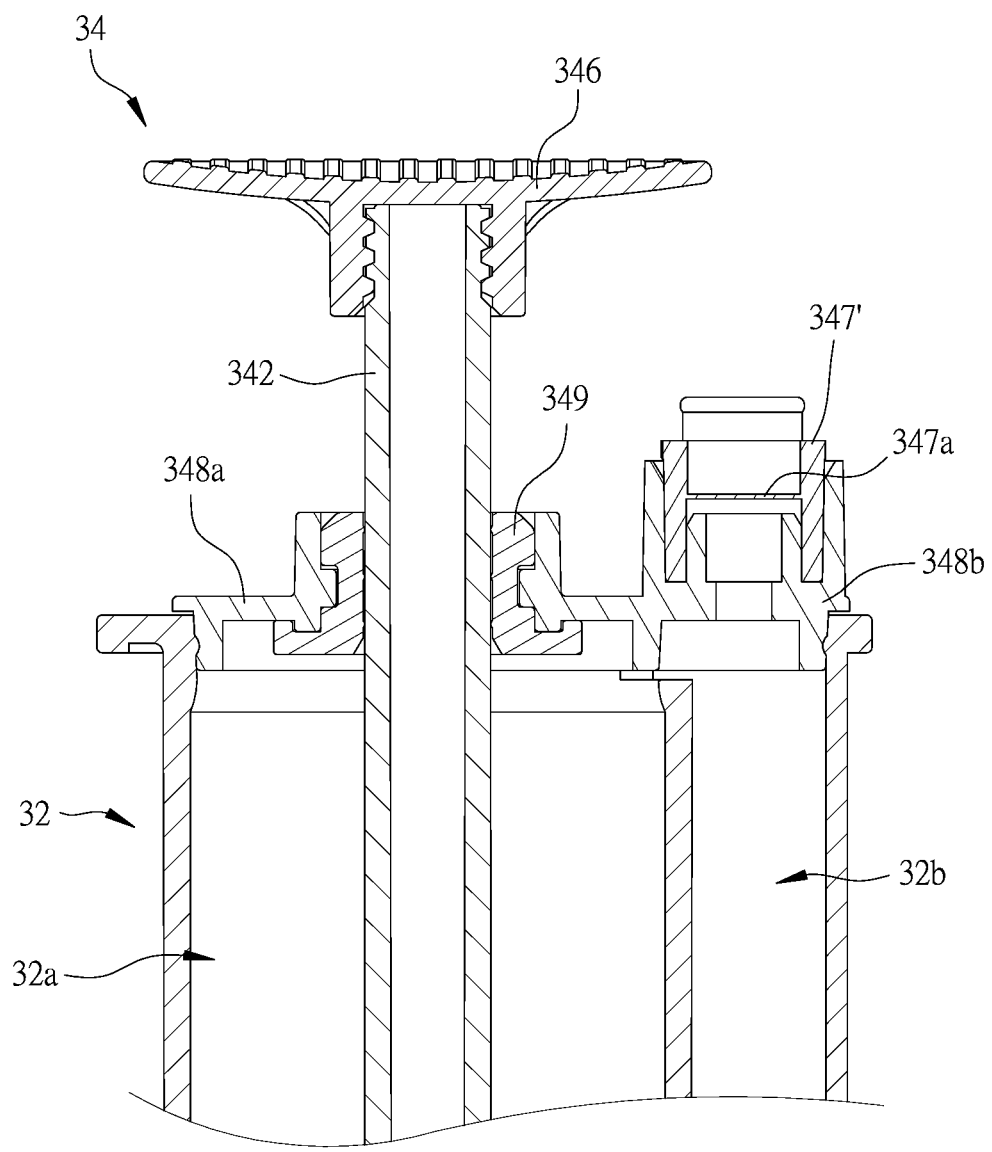

The plunger 34 includes a rod body 342, a piston 344, an operating member 346, and a sealing cap, wherein the sealing cap is fixed at a first end opening of the barrel 32, wherein the sealing cap seals the first end opening of the barrel 32. A means of sealing includes adhering and high-frequency welding. In the third embodiment, the sealing cap includes a first portion 348a and a second portion 348b, which are adjacently connected. The first portion 348a of the sealing cap corresponds to and covers the first cavity 32a. The first portion 348a includes a perforation for being passed through by the rod body 342, wherein the rod body 342 is controllable to move within the first cavity. In the third embodiment, the plunger 34 includes a sealing ring 349 that fits around the rod body 342 and is located at the perforation of the first portion 348a of the sealing cap, as shown in FIG. 17-1. In the third embodiment, a connecting portion 348a1 of the first portion 348a of the sealing cap is tightly engaged with a first connected portion 32a1 of the tube wall of the barrel 32. A connecting portion 348b1 of the second portion 348b of the sealing cap is tightly engaged with a second connected portion 32b1 of the tube wall of the barrel 32. A means of sealing includes adhering and high-frequency welding.

The second portion 348b of the sealing cap corresponds to and covers the second cavity 32b. The second portion 348b includes a mouth and a plug lid 347, wherein the plug lid 347 is operably plugged into the mouth to create a closed environment. Besides, when the plug lid 347 is removed from the mouth, the second cavity 32b communicates with outside.

Figure 2:
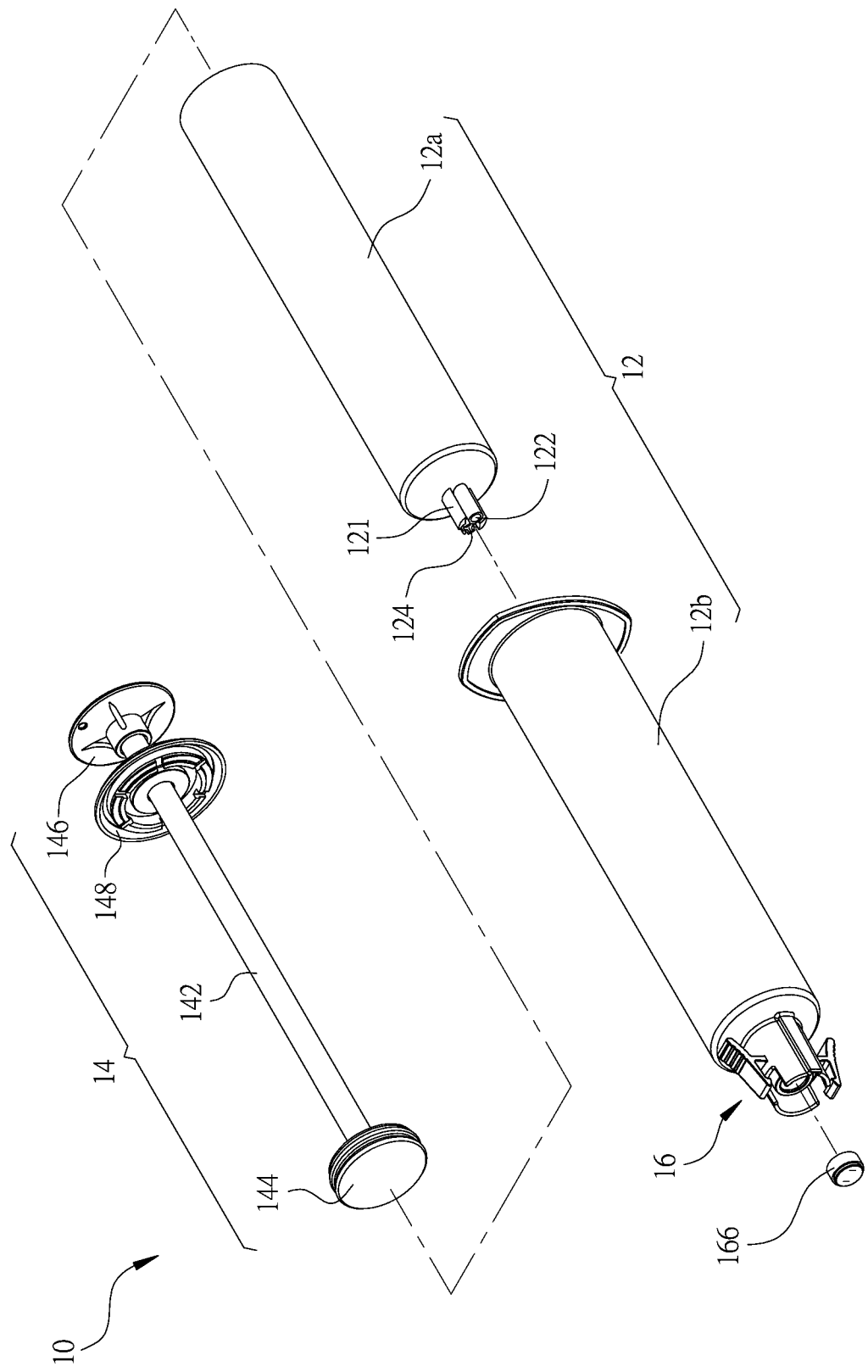
FIG. 2 is an exploded view of the closed system transfer device of the first embodiment according to the present invention.
Figure 3:
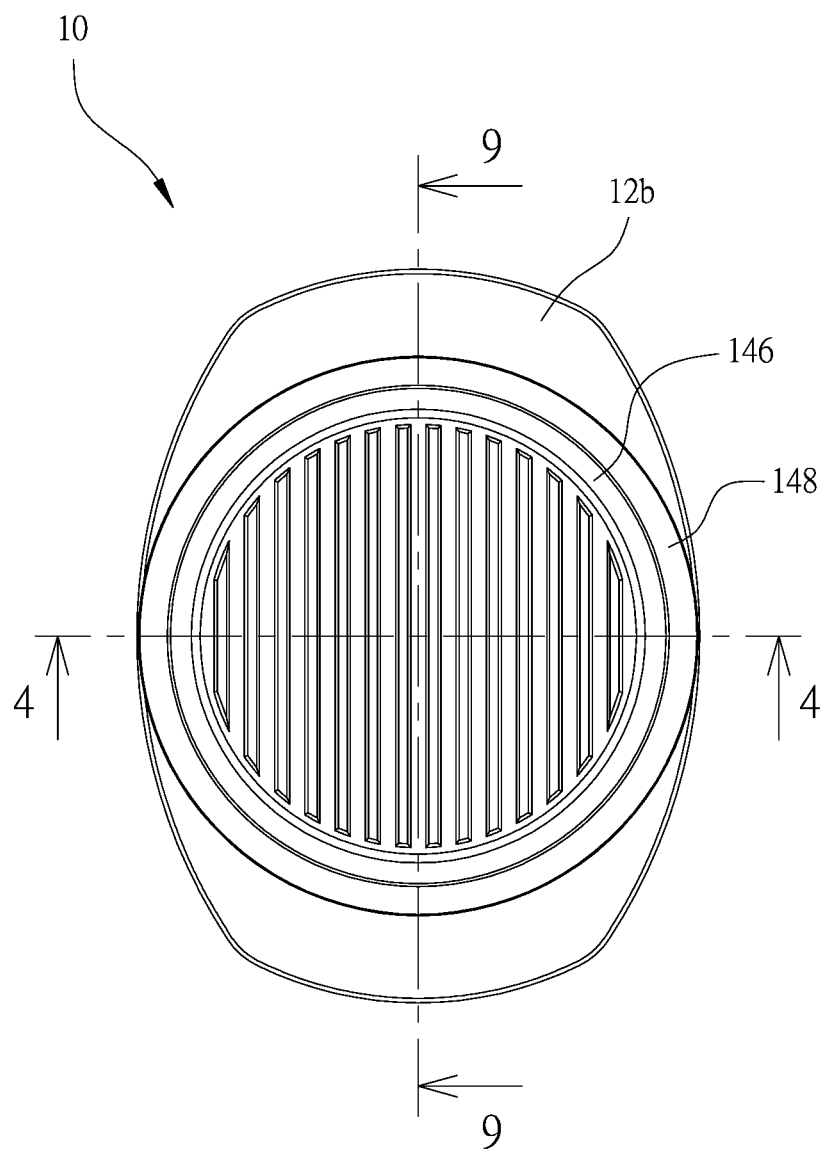
FIG. 3 is a top view of the closed system transfer device of the first embodiment according to the present invention.

FIG. 17-2 is similar to FIG. 17-1, the difference between FIG. 17-1 and FIG. 17-2 is that a plug lid 347' in FIG. 17-2 is a vent valve. The plug lid 347' has a lid and a filter paper 347a, wherein the lid is openable, and the filter paper 347a is disposed in the plug lid 347'.

The piston 344 is airtightly disposed in the first cavity 32a, and the piston 344 is operably moved within the first cavity 32a. The piston 344 divides the first cavity 32a into a first region and a second region, wherein the second region is closer to the first end opening of the barrel 32 than the first region. The second region does not communicate with the first region within the barrel 32, and the second region communicates with the second cavity at the first end opening. In the third embodiment, the first cavity 32a and a second cavity 32b has a first end opening. The sealing cap is fixed to the tube wall to seal the first end opening of the first cavity 32a and the second cavity 32. However, the sealing cap does not be connected to the isolating wall to seal or block the communication between the second region of the first cavity 32a and the second cavity 32b of the first end opening.

The connecting port 36 is fixed to a second end opening of the barrel 32, wherein the second end opening is opposite to the first end opening. The connecting port 36 includes a first channel 322, a second channel 324, and at least one soft plug 366. The first channel 322 communicates with the first cavity 32a, and the second channel 324 communicates with the second cavity 32b. The soft plug 366 is airtightly fixed to an end of the first channel 322 and an end of the second channel 324 to create a closed environment of the closed system transfer device 30.

When the closed system transfer device 30 is connected to a drug liquid container (not shown), the soft plug 366 could be operated to break. After the soft plug 366 is broken, the first channel 322 communicates with the second channel 324 via the drug liquid container. When the operating member 346 of the plunger 34 is pulled by an external force, the rod body 342 drives the piston 344 to move in a direction toward the first end opening of the barrel 32, so that the first region of the first cavity 32a is enlarged to draw a drug liquid in the drug liquid container into the first region through the first channel 322. Simultaneously, the second region is reduced, so that air in the second region is discharged to the drug liquid container through the second cavity 32b and the second channel 324. Thus, the closed system transfer device 30 and the drug liquid container form another closed environment.

The connecting port 36 includes at least one protruding column, wherein the protruding column is fixed to the second end opening of the barrel 32. The first channel 322 and the second channel 324 are disposed in the protruding column. The soft plug 366 is airtightly fixed to an end of the protruding column, which is away from the barrel 32. In the third embodiment, the protruding column includes a first protruding column 362a and a second protruding column 362b. The first channel 322 is disposed in the first protruding column 362a, and the second channel 324 is disposed in the second protruding column 362b. The soft plug 366 is airtightly fixed to an end of the first protruding column 362a and an end of the second protruding column 362b, which are away from the barrel 32. The first protruding column 362a and the second protruding column 362b are fixed to the second end opening of the tube body of the barrel 32. In the third embodiment, the soft plug 366 includes a first soft plug and a second soft plug. The first soft plug is airtightly fixed to an end of the first protruding column 362a, which is away from a barrel 32. The second soft plug is airtightly fixed to an end of the second protruding column 362b, which is away from a barrel 32. The first protruding column 362a and the second protruding column 362b are fixed to the second end opening of the barrel 32. The first channel 322 in the first protruding column 362a corresponds to and communicates with the first cavity 32a of the barrel 32. The second channel 324 of the second protruding column 362b corresponds to the second cavity 32b of the barrel 32 to communicate the second channel 324 and the second cavity 32b. As illustrated in FIG. 15, the soft plug 366 has two pin holes 366a, 366b, wherein one 366a of the two pin holes communicates with the first channel 322, and the other one 366b of the two pin holes communicates with the second channel 324. The connecting port 36 includes an annular wall 363, and a receiving groove 364 is formed between the first protruding column 362a, the second protruding column 362b, and the annular wall 363.

Figure 7:
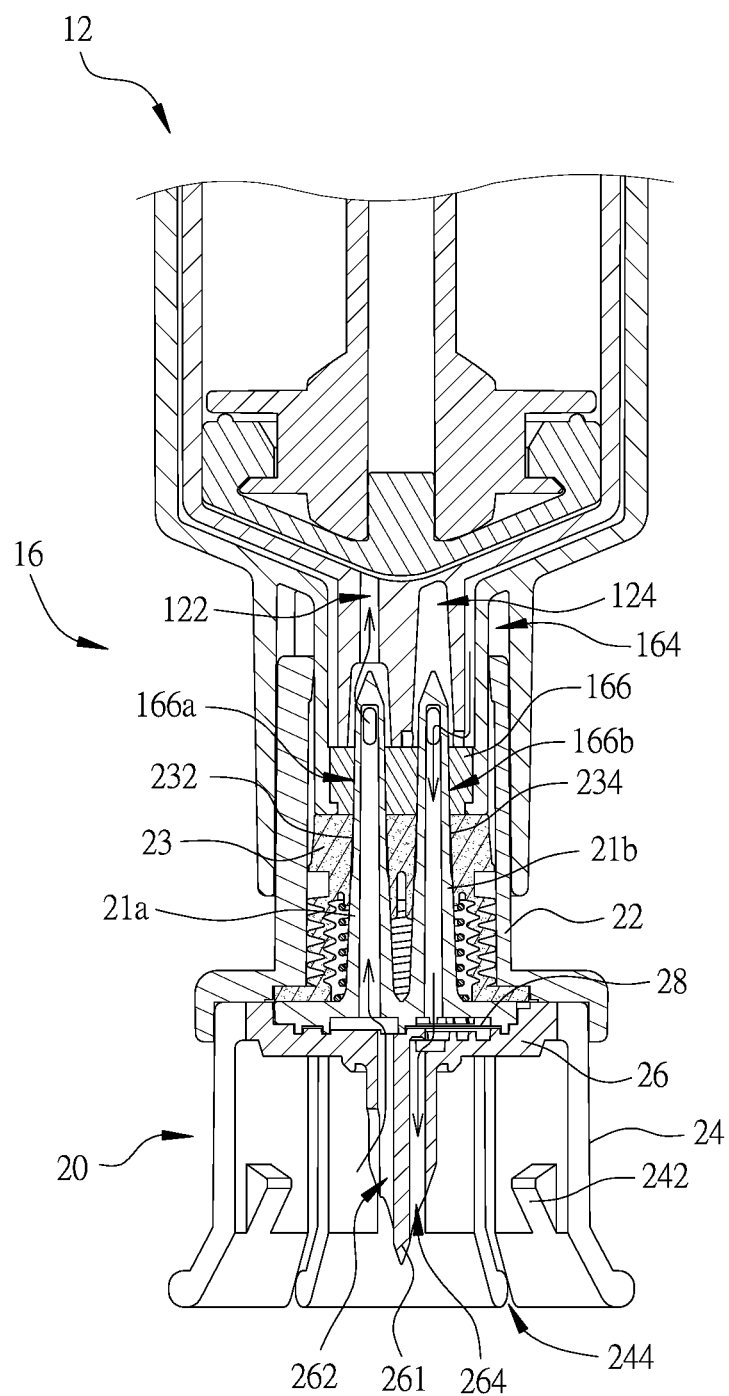
FIG. 7 is an enlarged partial view of the connecting port in FIG. 5, showing the connecting port is engaged with the hub.

As illustrated in FIG. 7, FIG. 10, and FIG. 18 to FIG. 22, a hub 20 of a fourth embodiment according to the present invention is detachably connecting to the connecting port 16. The hub 20 includes a first end portion 22 and a second end portion 24, which are opposite to each other. The first end portion 22 includes a first needle 21a and a second needle 21b, wherein the first needle 21a and the second needle 21b extend in the same direction and are adjacent to each other. When the first end portion 22 of the hub 20 is connected to the connecting port 16, the first needle 21a and the second needle 21b are inserted through the soft plug 166 to allow the first needle 21a to be inserted into the first channel 122, and the second needle 21b to be inserted into the second channel 124, as shown in FIG. 7. The second end portion 24 of the hub 20 is detachably connected to the drug liquid container and communicates with the first needle 21a of the first end portion 22.

Figure 20:
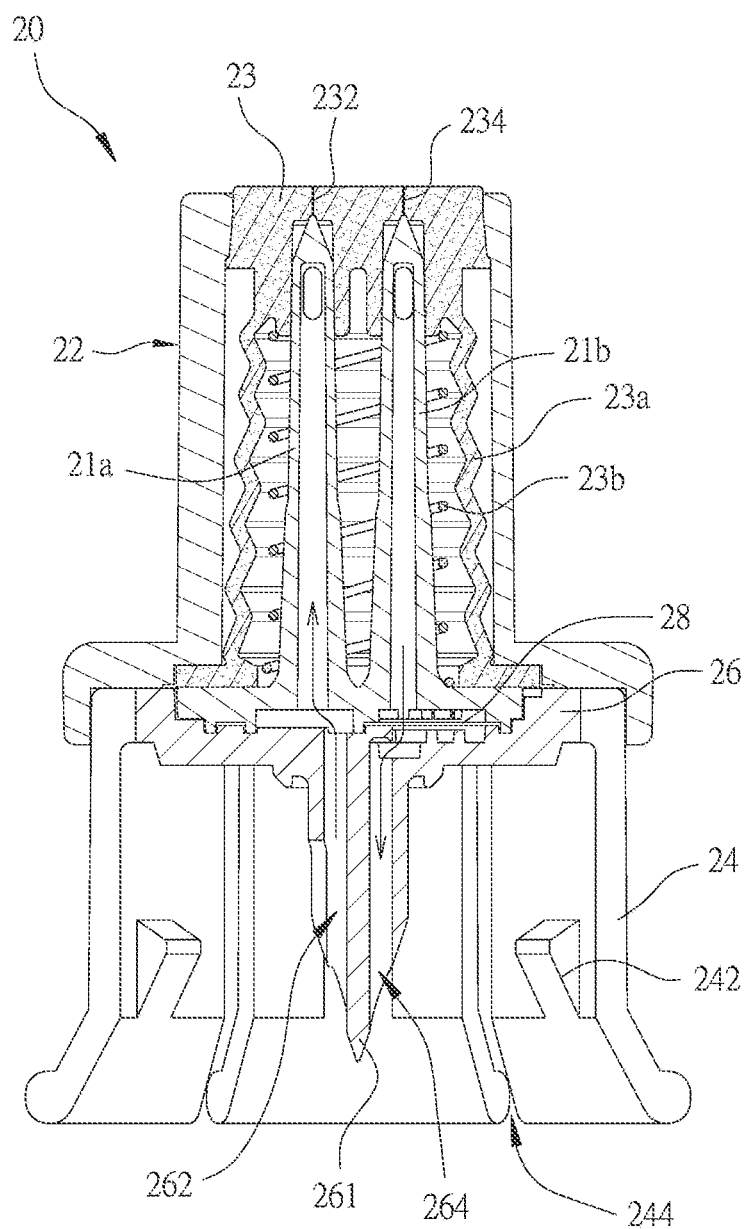
FIG. 20 is a section view taken along the 20-20 line in FIG. 19.
Figure 21:
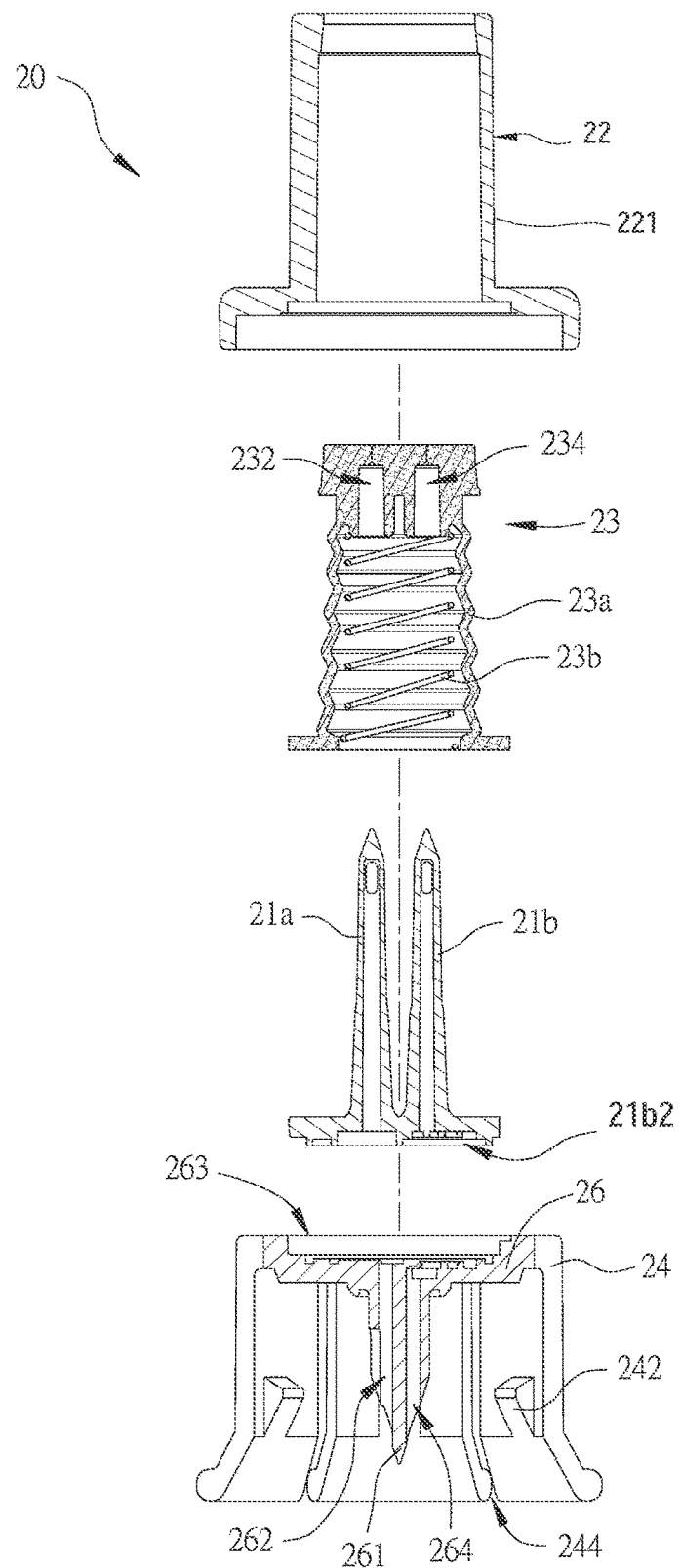
FIG. 21 is an exploded view of FIG. 20.

As illustrated in FIG. 20, the first end portion 22 includes a hollowed column 221 and an elastic member 23, wherein the first needle 21a, the second needle 21b, and the elastic member 23 are located in the hollowed column 221. When the hub 20 does not be connected to the connecting port 16, the elastic member 23 covers the first needle 21a and the second needle 21b to avoid the first needle 21a and the second needle 21b being exposed outside. In the fourth embodiment, a longitudinal direction of the hollowed column 221 is parallel to a longitudinal direction of the first needle 21a and the second needle 21b. When the hub 20 is connected to the connecting port 16, the elastic member 23 could be pressed. Specifically, when the hub 20 is connected to the connecting port 16, the elastic member 23 is operably pressed along the longitudinal direction of the hollowed column 221 toward the second end portion 24 to allow the first needle 21a and the second needle 21b to protrude out of the elastic member 23 and insert through the soft plug 166.

Figure 18:
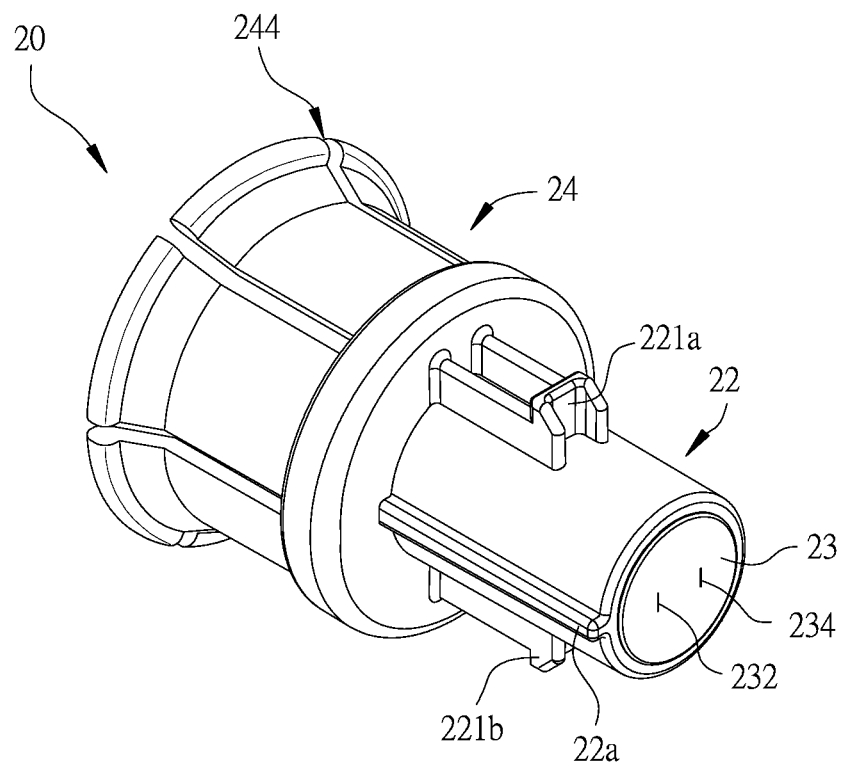
FIG. 18 is a perspective view of the hub of a fourth embodiment according to the present invention.
Figure 19:
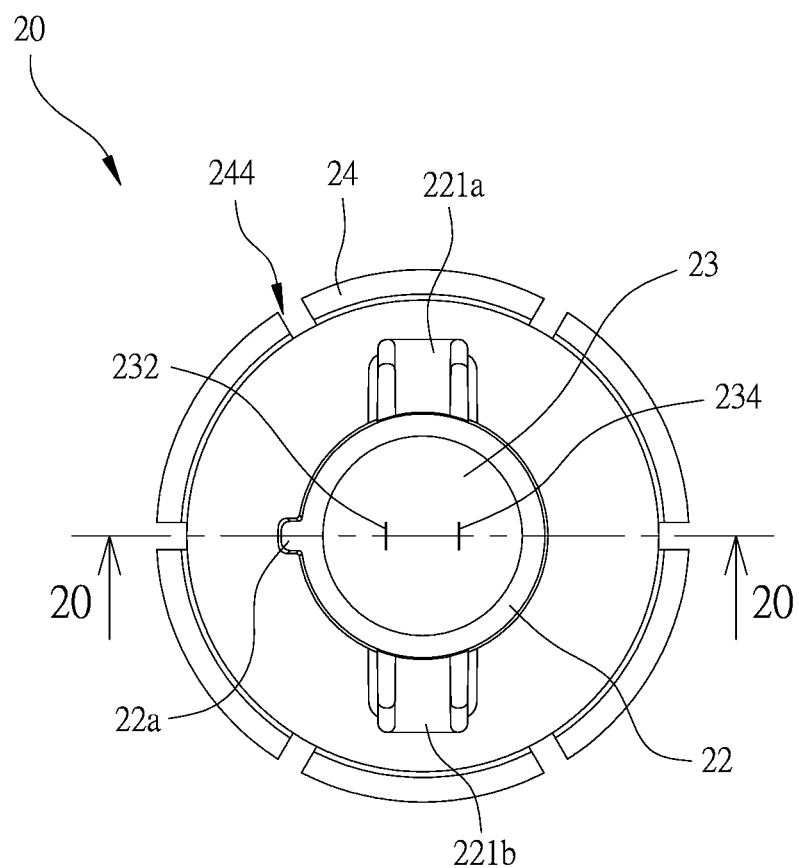
FIG. 19 is a top view of the hub of the fourth embodiment according to the present invention.

In the fourth embodiment, the elastic member 23 includes an external elastomer 23a and an internal elastomer 23b, wherein the external elastomer 23a covers the internal elastomer 23b, and the external elastomer 23a is located between the hollowed column 221 and the internal elastomer 23b. As illustrated in FIG. 18, the elastic member 23 has two pin holes 232, 234, wherein one 232 of the two pin holes corresponds to the first needle 21a, and the other one 234 of the two pin holes corresponds to the second needle 21b. When the hub 20 does not be connected to the connecting port 16, the internal elastomer 23b surrounds the first needle 21a and the second needle 21b, and the external elastomer 23a covers the first needle 21a and the second needle 21b. When the hub 20 is connected to the connecting port 16, the external elastomer 23a and the internal elastomer 23b are pressed by the connecting port 16 to move along the longitudinal direction of the hollowed column 221 toward the second end portion 24, so that the first needle 21a and the second needle 21b protrude out of the external elastomer 23a and insert through the soft plug 166.

It is worthy to mention that when the hub 20 is disengaged from the connecting port 16, the external elastomer 23a and the internal elastomer 23b rebound along the longitudinal direction of the hollowed column 221 away from the second end portion 24. During the disengagement process, the internal elastomer 23b urges the external elastomer 23a to continuously contact with the connecting port 16, so that the first needle 21a and the second needle 21b do not be exposed outside, thereby avoiding a user being hurt by the first needle 21a and the second needle 21b.

The connecting port 16 includes an annular wall 163, wherein a receiving groove 164 is formed between the annular wall 163 and the sleeve body 161. The annular wall 163 is adapted to correspondingly fit around the hollowed column 221. An inner circumference of the annular wall 163 includes a slot 16a, and an outer circumference of the hollowed column 221 includes a rib 22a. When the annular wall 163 correspondingly fits around the hollowed column 221, the slot 16a is engaged with the rib 22a to guide the first needle 21a to insert into the first channel 122 and the second needle 21b to insert into the second channel 124, thereby avoiding the first needle 21a to be inserted into the second channel 124 and the second needle 21b to be inserted into the first channel 122, as shown in FIG. 1 to FIG. 7.

Figure 10:
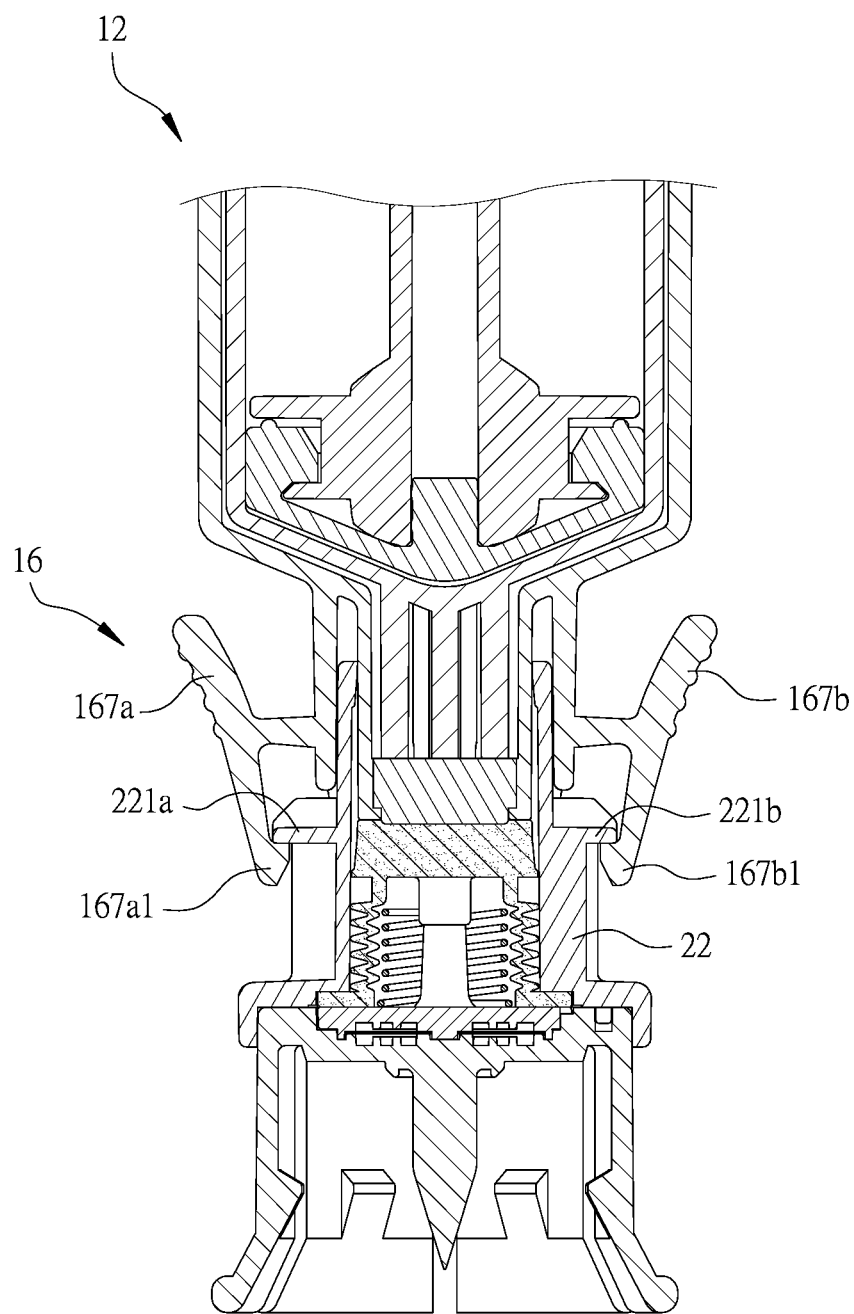
FIG. 10 is an enlarged partial view of the connecting port in FIG. 5, showing the connecting port is engaged with the hub.
Figure 11:
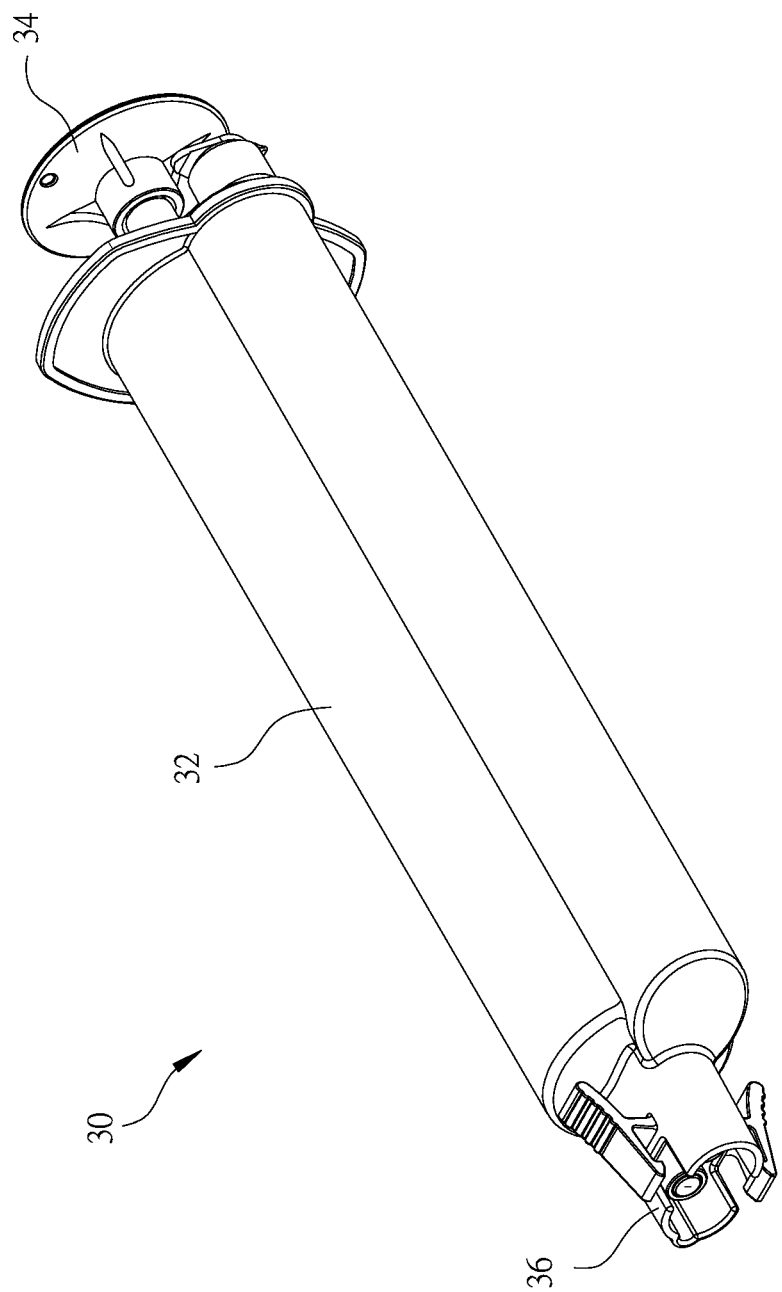
FIG. 11 is a perspective view of the closed system transfer device of a third embodiment according to the present invention.
Figure 12:
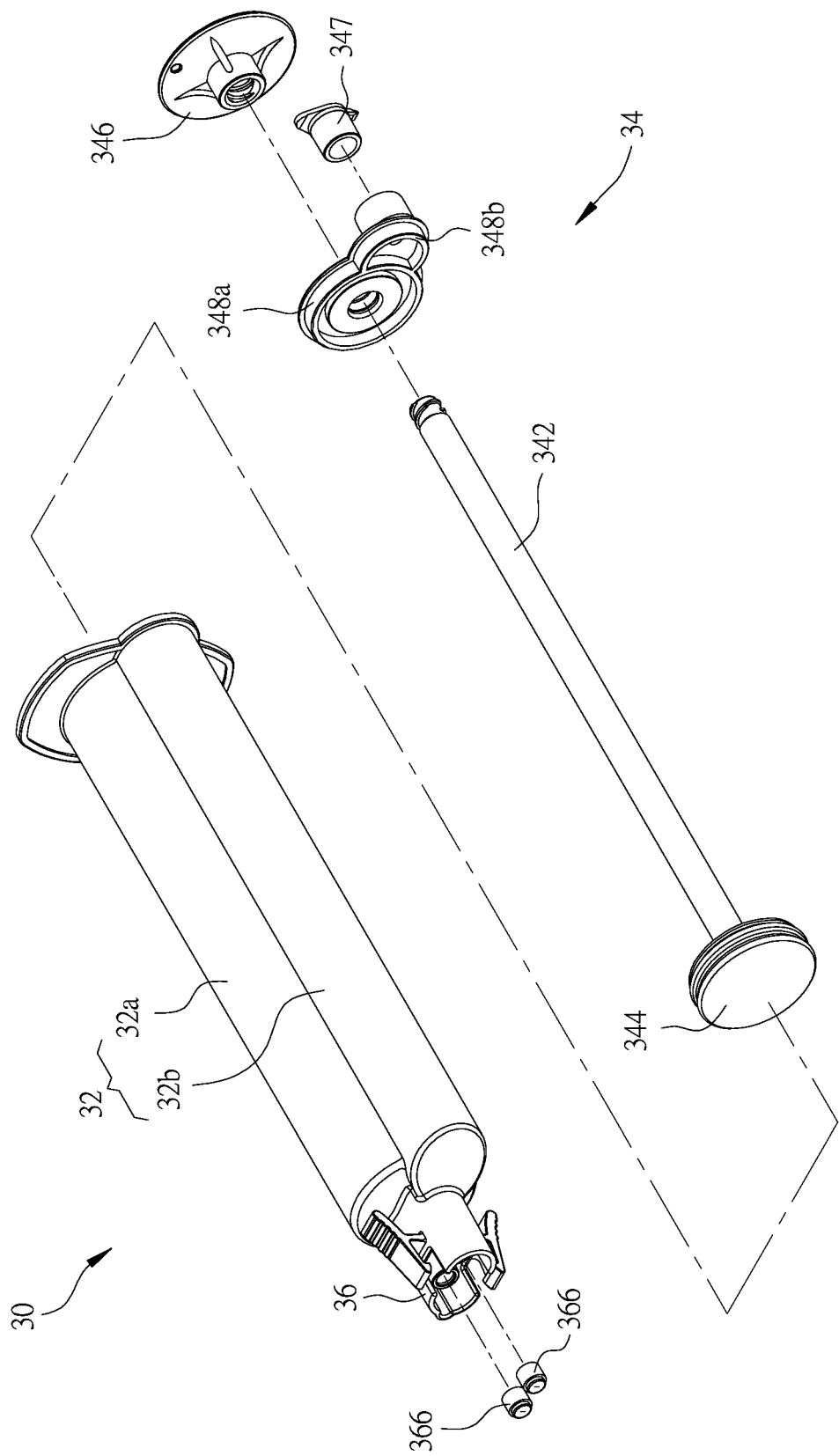
FIG. 12 is an exploded view of the closed system transfer device of the third embodiment according to the present invention.
Figure 13:
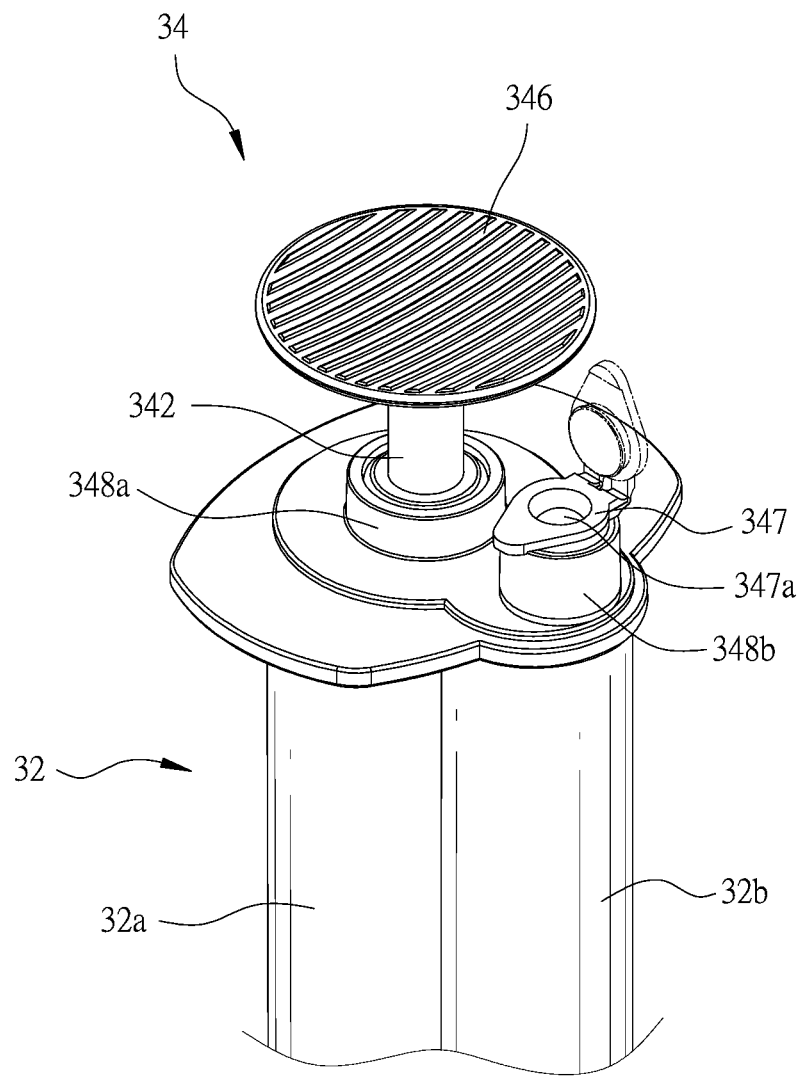
FIG. 13 is an enlarged partial view of the operating member and the sealing cap in FIG. 12.
Figure 14:
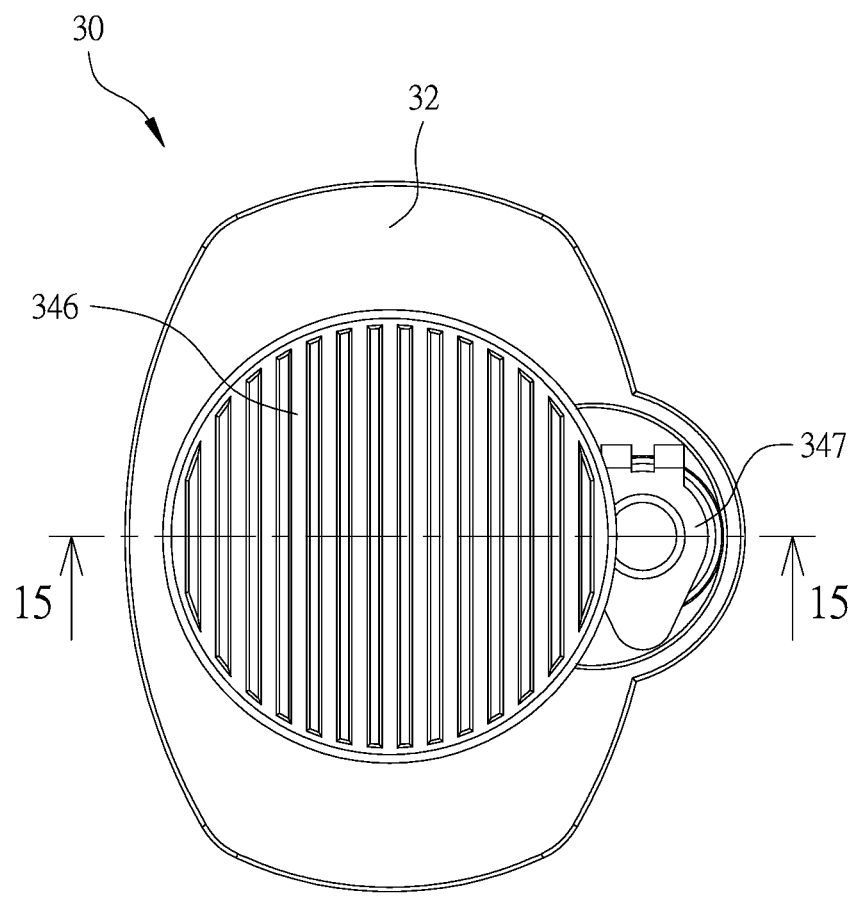
FIG. 14 is a top view of the closed system transfer device of a third embodiment according to the present invention.

An outer circumference of the annular wall 163 includes at least one hooking member, and the outer circumference of the hollowed column 221 includes at least one hooked member. In the current embodiment, the at least one hooking member includes two hooking members 167a, 167b, wherein the at least one hooked member includes two hooked members 22a, 22b. When the annular wall 163 correspondingly fits around the hollowed column 221, a hook end 167a1, 167b1 of each of the two hooking members 167a, 167b is engaged with one of the two hooked members 22a, 22b, thereby firmly engaging the hub 20 with the connecting port 16, as illustrated in FIG. 10.

The second end portion 24 of the hub 20 includes a lancet 26, wherein the lancet 26 could detachably connected to the drug liquid container. The lancet 26 includes a first pathway 262 and a second pathway 264, which are separated from each other, wherein the first pathway 262 communicates with the first needle 21a, and the second pathway 264 communicates with the second needle 21b, as illustrated in FIG. 20. In the fourth embodiment, an opening of the first pathway 262 of the lancet 26 extends in a direction from a tip 261 to a root of the lancet 26. In the fourth embodiment, the opening of the first pathway 262 of the lancet 26 is greater than an opening of the second pathway 264

The hub 20 includes a filter paper 28, wherein the filter paper 28 is disposed between the second pathway 264 and the second needle 21b, so that the drug liquid is prevented from flowing into the second pathway 264 through the second needle 21b, thereby avoiding the drug liquid to enter the second cavity 162 of the barrel 12, which is provided for airflow, as shown in FIG. 4. Additionally, the filter paper 28 could be used for filtering out the impurities of the air in the closed system transfer device 10.

In the fourth embodiment, the second end portion 24 includes a ferrule, wherein the ferrule is detachably connected to the drug liquid container. The ferrule includes a plurality of elastic plates that are arranged to form a cylinder and are spaced apart from each other. A gap 244 is formed between the adjacent two of the elastic plates. The elastic plates are adapted to receive the drug liquid containers with different outer diameters. Each of the elastic plates includes a protruding edge 242, the protruding edge 242 is adapted to be engaged with an external surface of the drug liquid container.

Figure 22:
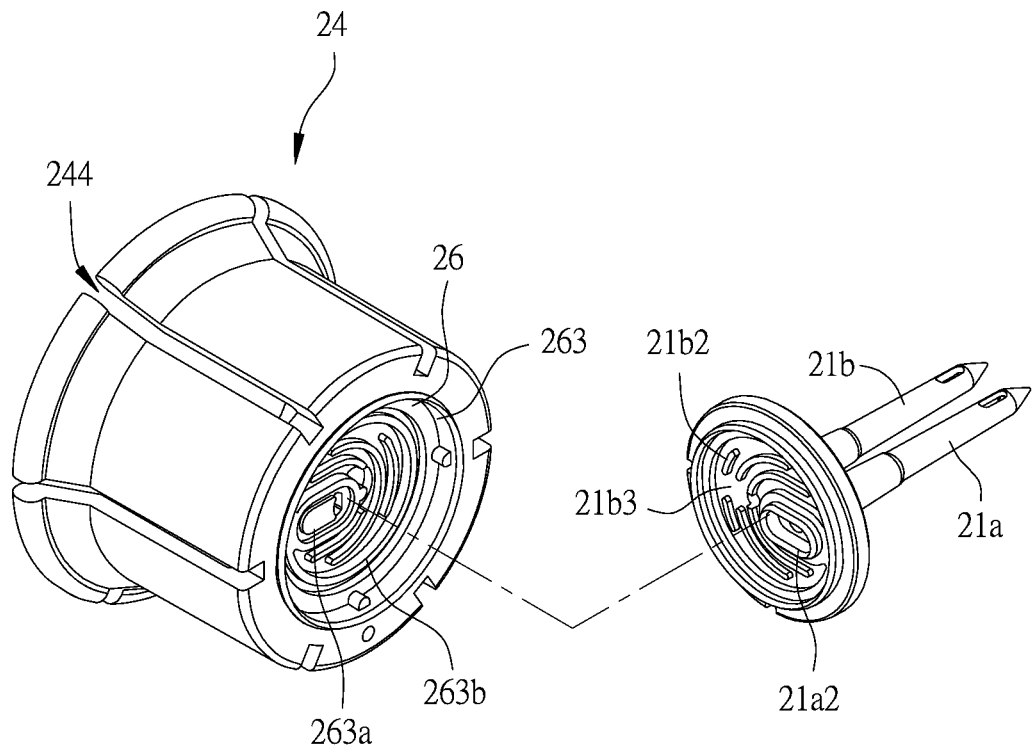
FIG. 22 is an exploded view, showing the second needle of the first end portion is disengaged with the second end portion of the hub of the fourth embodiment.

As illustrated in FIG. 22, a bottom 21a2 of the first needle 21a is correspondingly connected to a communicating hole 263a of the lancet 26. A bottom of the second needle 21b includes a plurality of short walls 21b2 and a flow channel 21b3, wherein the short walls 21b2 and the flow channel 21b3 are correspondingly connected to a plurality of short walls 263b in the recess 263 of the lancet 26 to form a curved channel between the lancet 26 and the second needle 21b, thereby preventing the drug liquid from flowing too fast to break the filter paper 28.

As illustrated in FIG. 23 to FIG. 28, a hub 40 of a fifth embodiment is detachably connected to the connecting port 16. The hub 40 includes a first end portion 42 and a second end portion 44, which are opposite to each other. The first end portion 42 includes a first needle 41a and a second needle 41b, wherein the first needle 41a and the second needle 41b extend in the same direction and are adjacent to each other. When the first end portion 42 of the hub 40 is connected to the connecting port 16, the first needle 41a and the second needle 41b are inserted through the soft plug 166 to allow the first needle 41a to be inserted into the first channel 122, and the second needle 41b to be inserted into the second channel 124. The second end portion 44 of the hub 40 is detachably connected to the drug liquid container and communicates with the first needle 41a of the first end portion 42.

Figure 23:
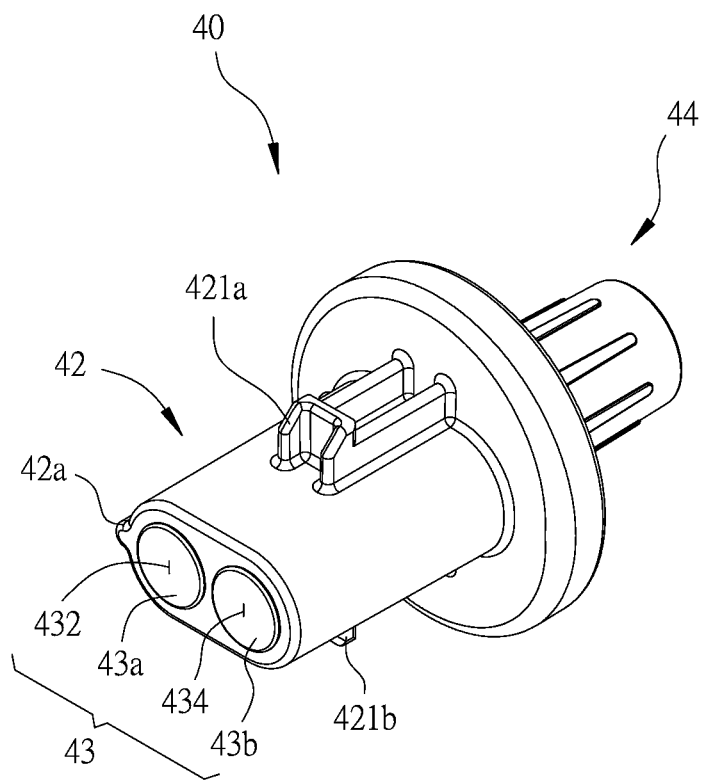
FIG. 23 is a perspective view of the hub of a fifth embodiment according to the present invention.
Figure 24:
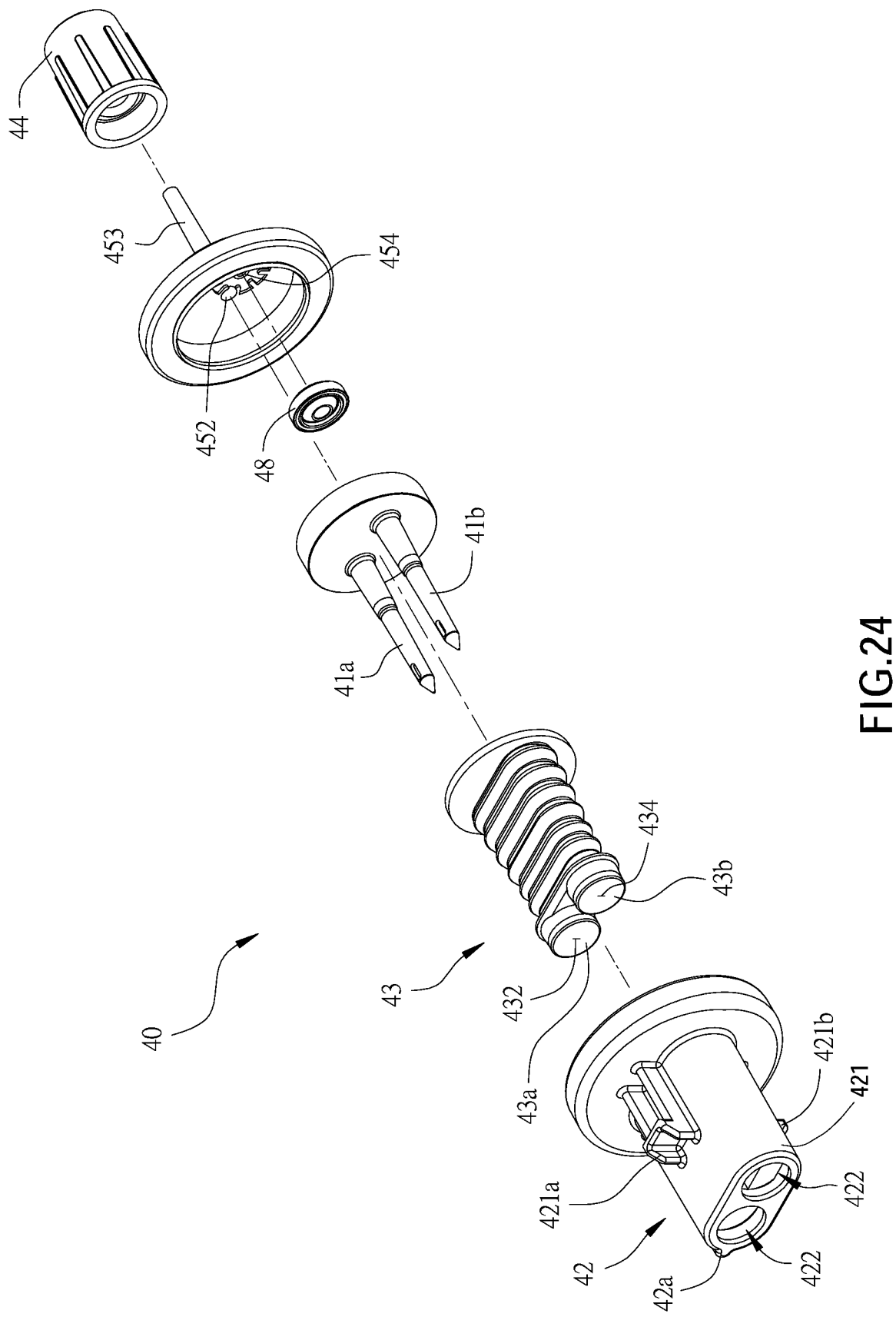
FIG. 24 is an exploded view of the hub of the fifth embodiment according to the present invention.
Figure 25:
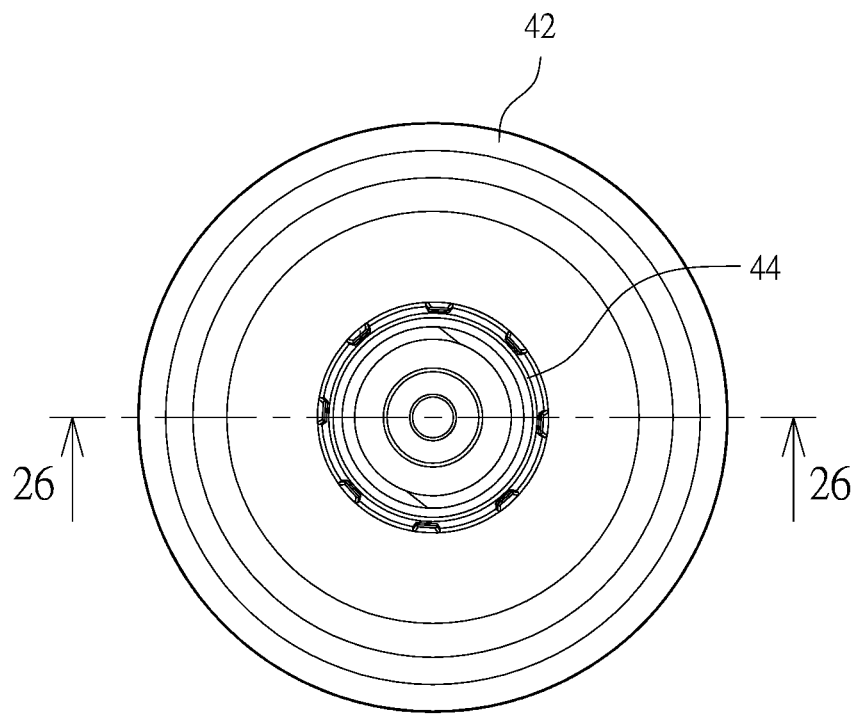
FIG. 25 is a top view of the hub of the fifth embodiment according to the present invention.
Figure 26:
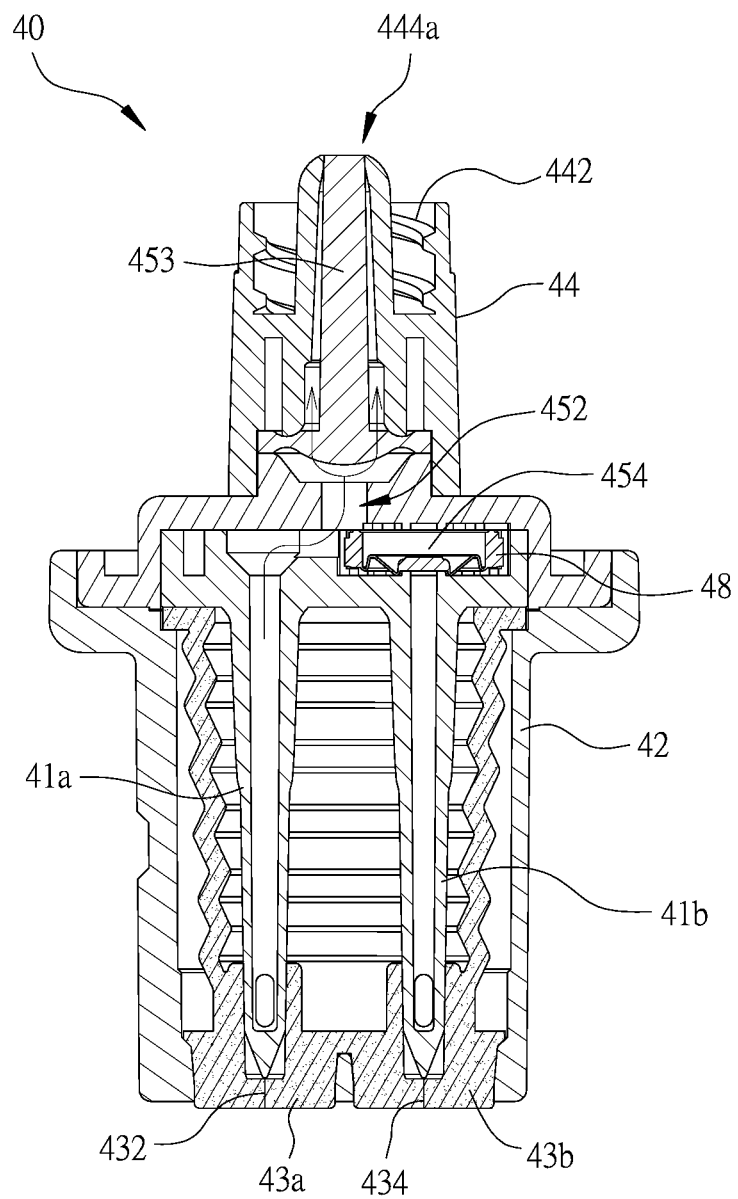
FIG. 26 is a section view taken along the 26-26 line in FIG. 25.

As illustrated in FIG. 24, the first end portion 42 includes a hollowed column 421 and an elastic member 43, wherein the first needle 41a, the second needle 41b, and the elastic member 43 are located in the hollowed column 421. As illustrated in FIG. 23, the elastic member 43 includes a first elastic member 43a and a second elastic member 43b, wherein the first elastic member 43a has a pin hole 432, and the second elastic member 43b has a pin hole 434. The pin hole 432 of the first elastic member 43a corresponds to the first needle 41a, and the pin holes 434 of the second elastic member 43b corresponds to the second needle 41b. As illustrated in FIG. 24, the hollowed column 421 includes two through holes 422, wherein one of the two through holes 422 corresponds to the first elastic member 43a, and the other one of the two through holes 422 corresponds to the second elastic member 43b. When the hub 40 is not connected to the connecting port 16, the elastic member 43 covers the first needle 41a and the second needle 41b to avoid the first needle 41a and the second needle 41b being exposed outside. In the fifth embodiment, a longitudinal direction of the hollowed column 421 is parallel to a longitudinal direction of the first needle 41a and the second needle 41b. When the hub 40 is connected to the connecting port 16, the elastic member 43 could be pressed. Specifically, when the hub 40 is connected to the connecting port 16, the elastic member 43 is operably pressed along the longitudinal direction of the hollowed column 421 toward the second end portion 44 to allow the first needle 41a and the second needle 41b to protrude out of the elastic member 43 and insert through the soft plug 166.

The connecting port 16 includes an annular wall 163, wherein a receiving groove 164 is formed between the annular wall 163 and the sleeve body 161. The annular wall 163 is adapted to correspondingly fit around the hollowed column 421. The inner circumference of the annular wall 163 includes a slot 16a, and an outer circumference of the hollowed column 421 includes a rib 42a. When the annular wall 163 correspondingly fits around the hollowed column 421, the slot 16a is engaged with the rib 42a to guide the first needle 41a to insert into the first channel 122 and the second needle 41b to insert into the second channel 124, thereby avoiding the first needle 41a to be inserted into the second channel 124 and the second needle 41b to be inserted into the first channel 122.

The outer circumference of the annular wall 163 includes at least one hooking member, and the outer circumference of the hollowed column 421 includes at least one hooked member. In the current embodiment, the at least one hooking member includes two hooking members 167a, 167b, wherein the at least one hooked member includes two hooked members 22a, 22b. When the annular wall 163 correspondingly fits around the hollowed column 421, the two hooking members 167a, 167b is respectively engaged with the two hooked members 42a, 42b, thereby firmly engaging the hub 40 with the connecting port 16.

Figure 27:
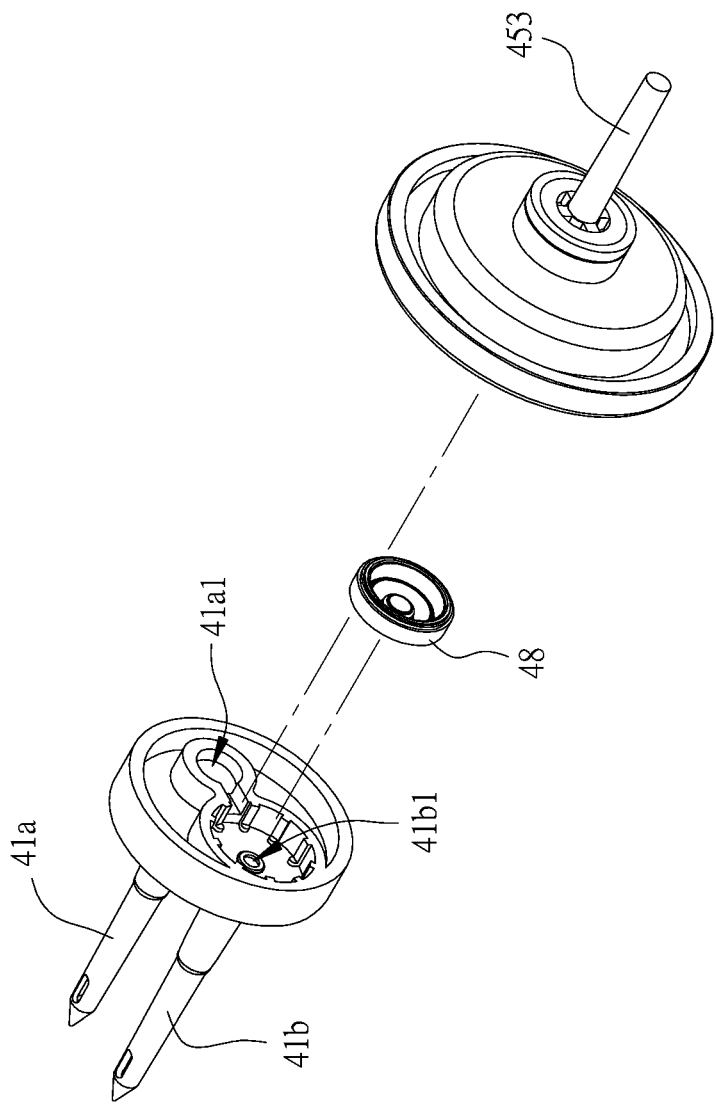
FIG. 27 is an exploded view, showing the second needle of the first end portion is disengaged from the second end portion, wherein the angle of view of FIG. 27 is a first perspective.
Figure 28:
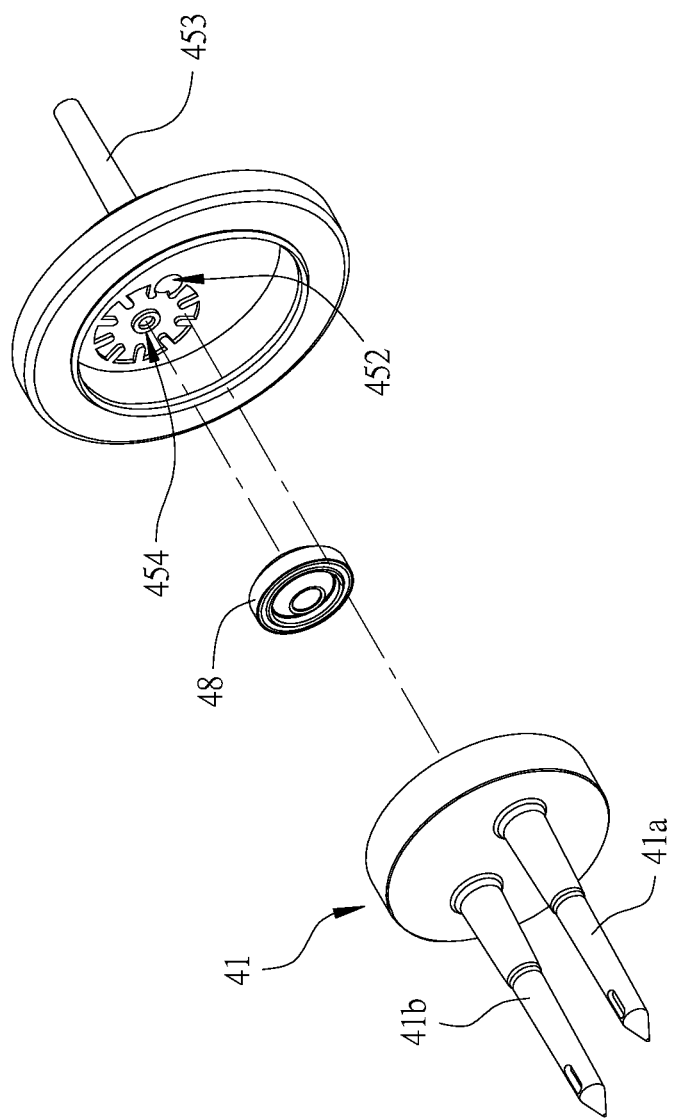
FIG. 28 is an exploded view, showing the second needle of the first end portion is disengaged from the second end portion, wherein the angle of view of FIG. 28 is a second perspective.
Figure 29:
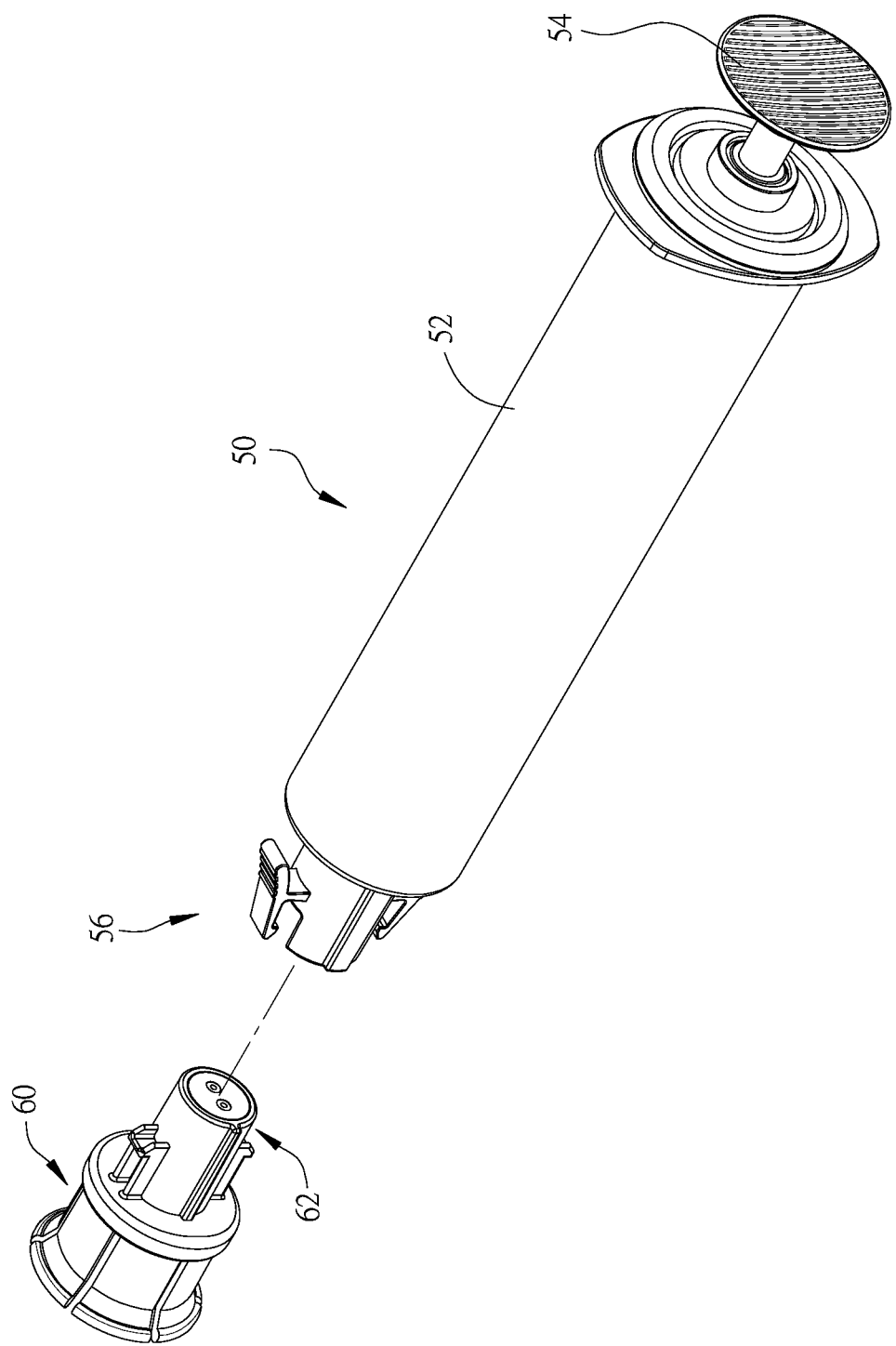
FIG. 29 is a perspective view of the closed system transfer device of a sixth embodiment according to the present invention.
Figure 30:
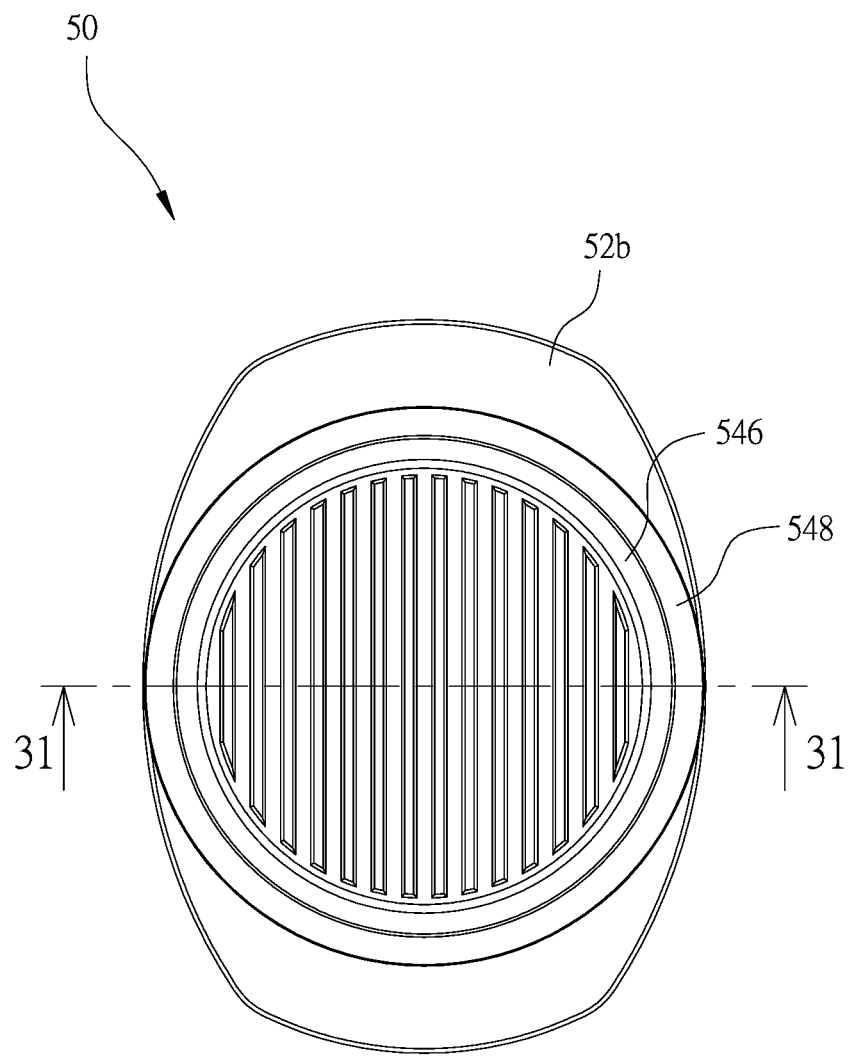
FIG. 30 is a top view of the closed system transfer device of the sixth embodiment according to the present invention.

As illustrated in FIG. 5, the second end portion 44 of the hub 40 includes an infusion needle 453 and a ferrule, wherein the infusion needle 453 includes a third pathway 444a, 452. The third pathway 444a communicates with the first needle 41a. As illustrated in FIG. 27, the bottom 41a1 of the first needle 41a communicates with the third pathway 444a, 452. The ferrule includes an internal thread 442 that is adapted to be detachably screwed with an external thread of the drug liquid container (not shown). The hub 40 includes an anti-reverse flow pad 48 disposed between the second end portion 44 and the second needle 41b. Furthermore, the anti-reverse flow pad 48 is correspondingly fixed between a recess 454 of the second end portion 44 of the hub 40 and a bottom 41b1 of the second needle 41b, so that the third pathway 444a is isolated from the second needle 41b to separate a pathway for air and a pathway for liquid (drug liquid), thereby preventing the drug liquid from flowing into the second cavity 162 of the barrel 12 in FIG. 4, which is provided for the airflow.

As illustrated in FIG. 29 to FIG. 33, a closed system transfer device 50 of a sixth embodiment according to the present invention includes a barrel 52, a plunger 54, and a connecting port 56.

Figure 31:
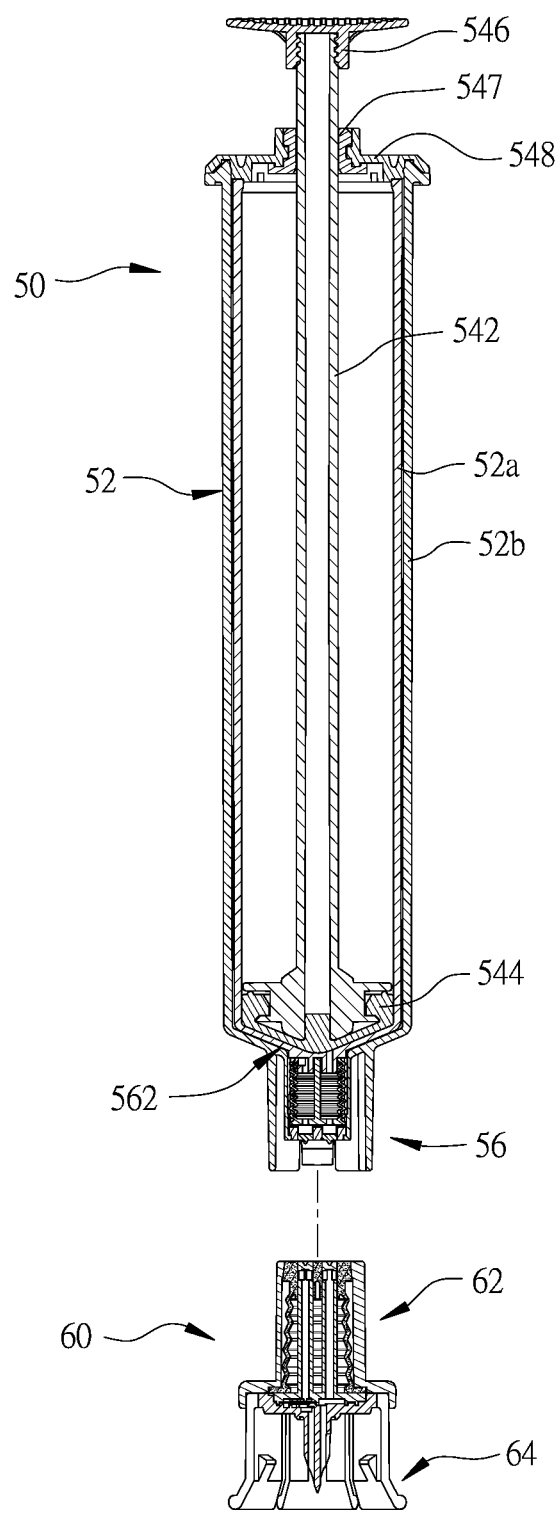
FIG. 31 is a sectional view taken along the 31-31 line in FIG. 30.

The barrel 52 includes a tube wall and an isolating wall, wherein the tube wall encircles to form a receiving space, and the isolating wall is disposed in the receiving space to form a first cavity and a second cavity, which are separated from each other. In the sixth embodiment, the tube wall is a first tube body 52b that has the receiving space, and the isolating wall encircles to form a second tube body 52a that is disposed in the receiving space of the first tube body 52b. A space encircled by the second tube body 52a constitutes the first cavity of the barrel 52, and a space formed between the first tube body 52b and the second tube body 52a constitutes the second cavity 562 of the barrel 12, as shown in FIG. 31.

The plunger 54 includes a rod body 542, a piston 544, an operating member 546, and a sealing cap 548, wherein the sealing cap 548 is fixed to and seals a first end opening of the barrel 52. In the sixth embodiment, a connecting portion of the sealing cap 548 is tightly connected to a connected portion of the first tube body 52b, wherein a means of connecting the connecting portion of the sealing cap 548 and the connected portion of the first tube body 52b includes adhering and high frequency welding. The rod body 542 passes through a perforation of the sealing cap 548. An end of the rod body 142 is connected to the operating member 546, and another end of the rod body 542 is connected to the piston 544. In the sixth embodiment, the plunger 54 includes a sealing ring 547 that fits around the rod body 542 and is located at the perforation of the sealing cap 148, as shown in FIG. 31. The piston 544 is airtightly disposed in the first cavity of the barrel 52 and is controllable to move within the first cavity. The piston 544 divides the first cavity into a first region and a second region, wherein the second region is closer to the first end opening of the barrel 52 than the first region. The first region does not communicate with the second region within the barrel 52. The second region communicates with the second cavity at the first end opening. In the sixth embodiment, the first tube body 52b has the first end opening, and the sealing cap 548 is fixed to the first end opening of the first tube body 12b to seal the first end opening, but the sealing cap 548 does not seal the second tube body 52a to allow the second region of the first cavity could communicate with the second cavity 562 at the first end opening.

The connecting port 56 is fixed to a second end opening of the barrel 52, wherein the second end opening is opposite to the first end opening. The connecting port 56 includes a first channel 522, a second channel 524, an elastic member 565, an anti-leakage ring 566, and at least one soft plug. In the current embodiment, the at least one soft plug includes a first soft plug 568a and a second soft plug 568b. The first channel 522 communicates with the first cavity, and the second channel 524 communicates with the second cavity 562. The anti-leakage ring 566 and the at least one soft plug are airtightly fixed to and seal an end of the first channel 522 and an end of the second channel 524 to create a closed environment of the closed system transfer device 50.

Figure 33:
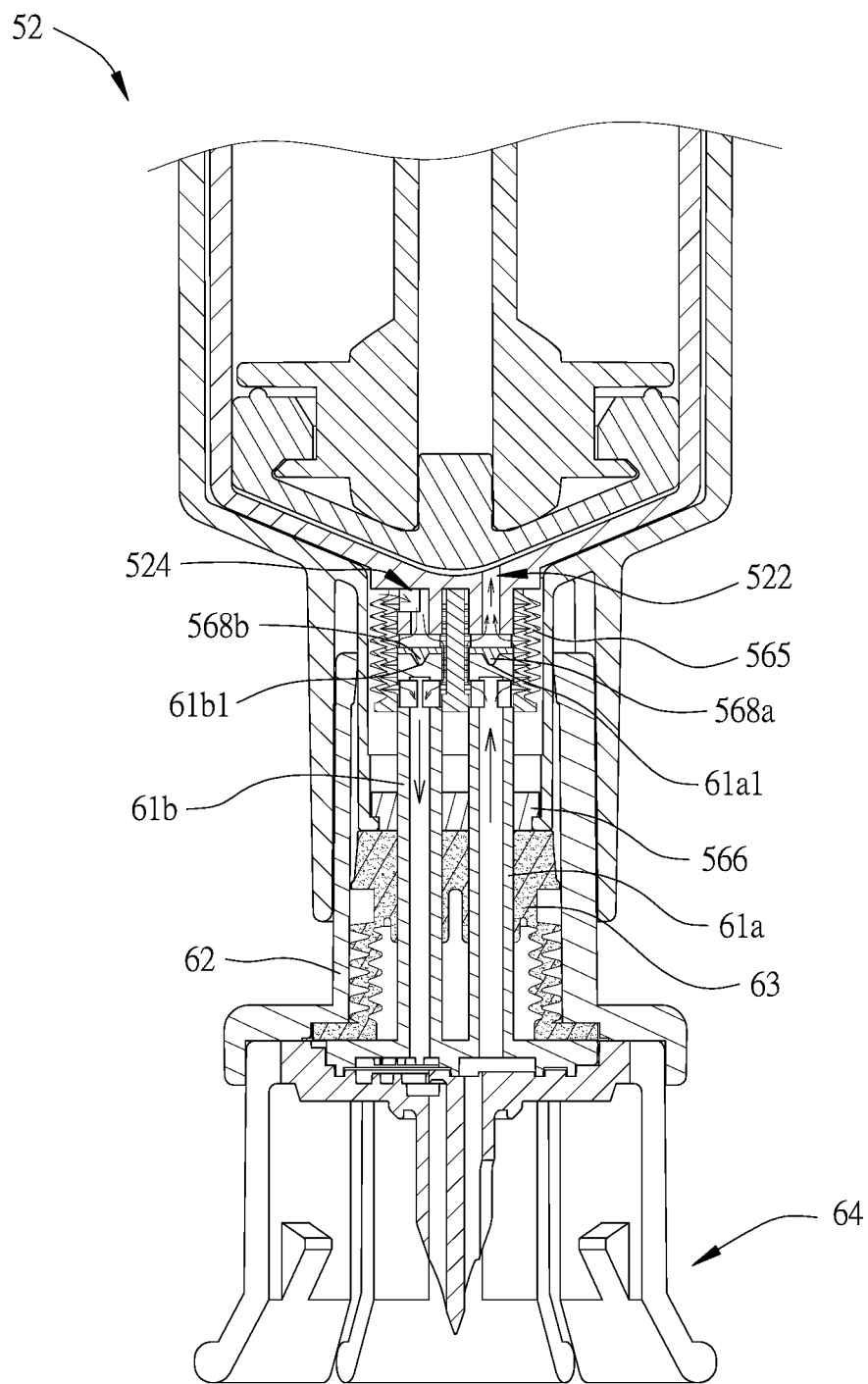
FIG. 33 is similar to FIG. 32, showing the hub is engaged with the connecting port.

The hub 60 of the sixth embodiment is detachably connected to the connecting port 56. The hub 60 includes a first end portion 62 and a second end portion 64, which are opposite to each other. The first end portion 62 includes a first needle 61*a* and a second needle 61*b*, wherein the first needle 61*a* and the second needle 61*b* extend in the same direction and are adjacent to each other. When the first end portion 62 of the hub 60 is connected to the connecting port 56, a top concave 61*a*1 of the first needle 61*a* urges against the first soft plug 568*a*, and a top concave 61*b*1 of the second needle 61*b* urges against the second soft plug 568*b*. Additionally, the first needle 61*a* correspondingly communicates with the first channel 522, and the second needle 61*b* correspondingly communicates with the second channel 524, as shown in FIG. 33. The second end portion 64 of the hub 60 is detachably connected to the drug liquid container (not shown) and communicates with the first needle 61*a* of the first end portion 62. In the sixth embodiment, when the first end portion 62 of the hub 60 is connected to the connecting port 56, the top concave 61*a*1 of the first needle 61*a* urges the first soft plug 568*a* and the top concave 61*b*1 of the second needle 61*b* urges the second soft plug 568*b*. Thus, the first and second soft plugs 568*a*, 568*b* urge the elastic member 565 to press the elastic member 565 in a direction toward the second end opening of the barrel 52.

Figure 32:
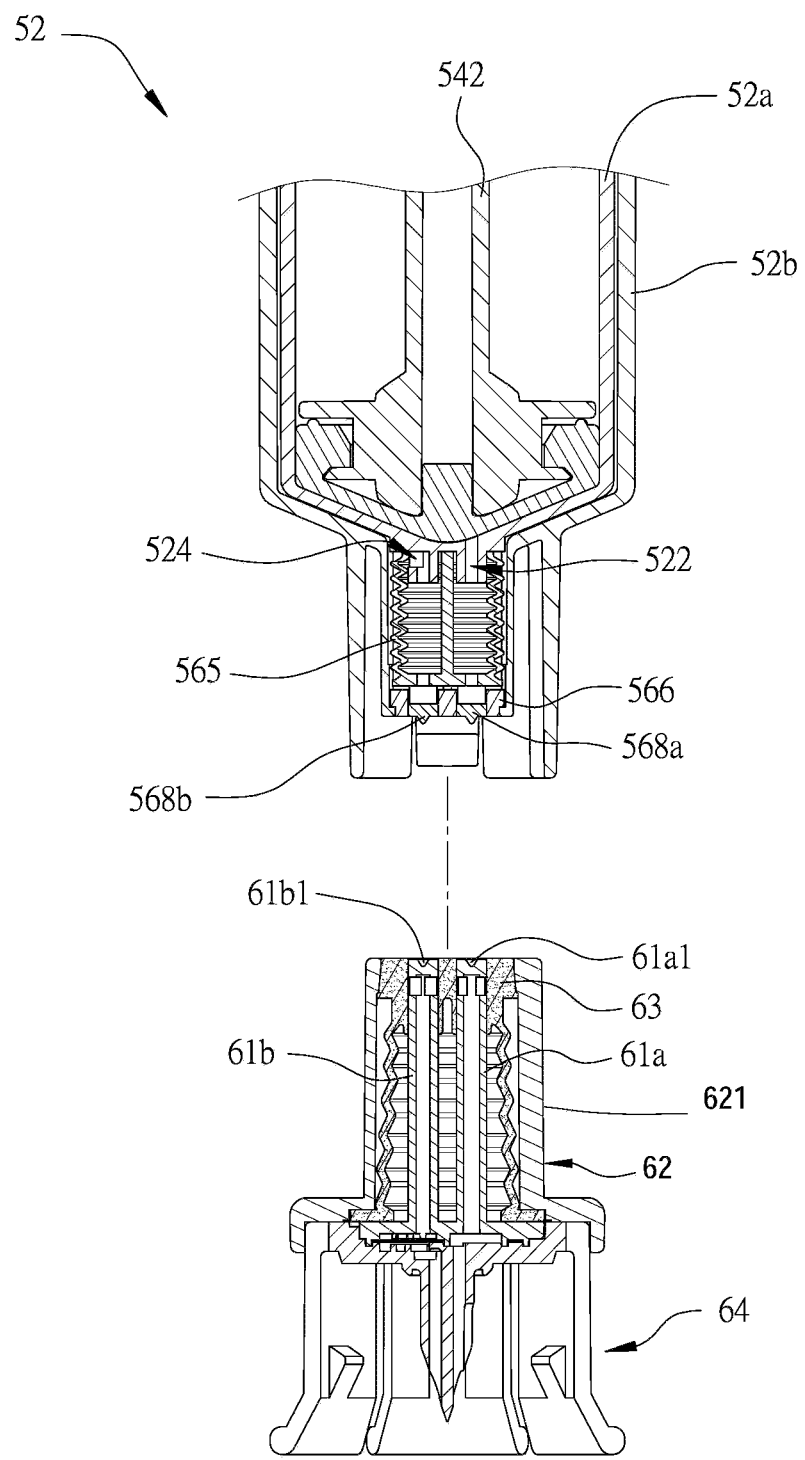
FIG. 32 is an enlarged partial view of the connecting port and the hub in FIG. 31, showing the hub is disengaged from the connecting port.

As illustrated in FIG. 32, the first end portion 62 includes a hollowed column 621 and an elastic member 63, wherein the first needle 61*a*, the second needle 61*b*, and the elastic member 63 are disposed in the hollowed column 621. When the hub 60 does not be connected to the connecting port 56, the elastic member 63 almost coves the first needle 61*a* and the second needle 61*b*, thereby preventing the drug liquid and/or air that remains in the first needle 61*a* and the second needle 61*b* from leaking out. In the sixth embodiment, the longitudinal direction of the hollowed column 621 is parallel to a longitudinal direction of the first needle 61*a* and the second needle 61*b*. When the hub 60 is connected to the connecting port 56, the elastic member 63 could be operably pressed along the longitudinal direction of the hollowed column 621 toward the second end portion 64, thereby allowing the first needle 61*a* and the second needle 61*b* to protrude out of the elastic member 63 and to abut against the first and the second soft plugs 568*a*, 568*b*. as shown in FIG. 33.

At the time, the second end portion 64 of the hub 60 is detachably connected to the drug liquid container, and the first channel 522 communicates with the second channel 524 via the drug liquid container. When the operating member 546 of the plunger 54 is pulled by an external force to drive the piston 544 to move toward the first end opening of the barrel 52 by the rod body 542, the first region of the first cavity is enlarged to draw the drug liquid in the drug liquid container through the first channel 522 into the first region. Simultaneously, the second region is reduced, and the air in the second region is discharged through the second cavity 562 and the second channel 524 to the drug liquid container. Therefore, the closed system transfer device 50 and the drug liquid container constitute another closed environment.

The closed system transfer device provided by the present invention does not include any needle that is exposed outside, so that the problem that the medical staff is hurt by the needle could be prevented, thereby reducing the risk of infection during the medical process. Additionally, the closed system transfer device provided by the present invention and the drug liquid container could constitute a closed environment. Therefore, when the drug liquid is volatile, the problem of concentration error and the risk of inhaling the volatile drug could be avoided, thereby enhancing the accuracy of operation and the health of the medical staff. Furthermore, the closed system transfer device provided by the present invention could avoid the possibility of using the same needle to draw different drug liquids, so that the drug liquids could be prevented from contaminating each other, thereby reducing the waste of the drug liquids.

It must be pointed out that the embodiment described above is only a preferred embodiments of the present invention. All equivalent structures and method which employ the concepts disclosed in this specification and the appended claims should fall within the scope of the present invention.

What is claimed is:

1. A closed system transfer device, comprising:
   a barrel comprising a tube wall and an isolating wall, wherein the tube wall encircles to form a receiving space, and the isolating wall is disposed in the receiving space to form a first cavity and a second cavity, which are separated from each other;
   a plunger comprising a sealing cap, a rod body, an operating member, and a piston, wherein the sealing cap is fixed to and seals a first end opening of the barrel, and the rod body passes through a perforation of the sealing cap; an end of the rod body is connected to the operating member, and another end of the rod body is connected to the piston; the piston is airtightly disposed in the first cavity of the barrel and is controllable to move within the first cavity; the piston divides the first cavity into a first region and a second region, wherein the second region is closer to the first end opening of the barrel than the first region; the first region does not communicate with the second region within the barrel; the second region communicates with the second cavity at the first end opening;
   a connecting port fixed to a second end opening of the barrel, wherein the second end opening is opposite to the first end opening; the connecting port comprises a first channel, a second channel, and at least one soft plug; the first channel communicates with the first cavity, and the second channel communicates with the second cavity; the at least one soft plug is airtightly fixed to an end of the first channel and an end of the second channel to create a closed environment of the closed system transfer device;
   wherein, when the closed system transfer device is connected to a drug liquid container, the at least one soft plug is operable to be broken to allow the first channel to communicate with the second channel via the drug liquid container; when the operating member of the plunger is pulled by an external force, the rod body drives the piston to move in a direction toward the first end opening of the barrel; the first region of the first cavity is enlarged to draw a drug liquid in the drug liquid container into the first region through the first channel; simultaneously, the second region is reduced, and air in the second region is discharged to the drug liquid container through the second cavity and the second channel, so that the closed system transfer device and the drug liquid container forms another closed environment.

2. The closed system transfer device as claimed in claim 1, wherein the tube wall is a first tube body that has the receiving space, and the isolating wall encircles to form a second tube body, and the second tube body is disposed in the receiving space of the first tube body; the second tube body constitutes the first cavity of the barrel, and a space formed between the first tube body and the second tube body constitutes the second cavity of the barrel.

3. The closed system transfer device as claimed in claim 2, wherein the first tube body has the first end opening, and the sealing cap is fixed to the first end opening of the first tube body to seal the first end opening, but the sealing cap does not seal the second tube body to allow the second region of the first cavity to communicate with the second cavity at the first end opening.

4. The closed system transfer device as claimed in claim 1, wherein the isolating wall is plate-shaped and is fixed to an inner side of the tube wall to divide the receiving space into a first cavity and a second cavity.

5. The closed system transfer device as claimed in claim 4, wherein the sealing cap is fixed at the first end opening of the barrel to seal the first end opening of the barrel, but the sealing cap does not seal the isolating wall to allow the second region of the first cavity to communicate with the second cavity at the first end opening.

6. The closed system transfer device as claimed in claim 4, wherein the sealing cap comprises a first portion and a second portion, which are connected to each other; the first portion of the sealing cap corresponds to and covers the first cavity; the first portion of the sealing cap comprises a perforation, wherein the rod body passes through the perforation of the first portion of the sealing cap and is controllable to move within the first cavity; the second portion of the sealing cap corresponds to and covers the second cavity; the second portion comprises a mouth and a plug lid, wherein the plug lid is operably plugged into or removed from the mouth; when the plug lid is plugged into the mouth, a closed environment is created; when the plug lid is removed from the mouth, the second cavity communicates outside.

7. The closed system transfer device as claimed in claim 6, wherein the plug lid comprises a filter paper, and the filter paper is used for filtering the air.

8. The closed system transfer device as claimed in claim 1, wherein the plunger comprises a sealing ring that fits around the rod body and is located at the perforation of the sealing cap.

9. The closed system transfer device as claimed in claim 1, wherein the connecting port comprises at least one protruding column, and the at least one protruding column is fixed to the second end opening of the barrel; the first channel and the second channel are disposed in the at least one protruding column; the at least one soft plug is airtightly fixed to an end of the protruding column, which is away from the barrel.

10. The closed system transfer device as claimed in claim 9, wherein the at least one protruding column is fixed to the second end opening of the second tube body of the barrel; the first channel in the at least one protruding column corresponds to and communicates with the first cavity; the connecting port comprises at least one sleeve body that receives the at least one protruding column; the at least one soft plug is airtightly clamped between the at least one protruding column and the at least one sleeve body; the at least one protruding column has a first side and a second side, which face opposite directions; the first channel is closer to the first side than the second side, and the second channel is closer to the second side than the first side; the at least one sleeve body has a first wall and a second wall, which face opposite directions; the first side of the at least one protruding column corresponds to the first wall of the at least one sleeve body; the second side of the at least one protruding column corresponds to the second wall of the at least one sleeve body.

11. The closed system transfer device as claimed in claim 9, wherein the at least one protruding column comprises a first protruding column and a second protruding column; the first channel is disposed in the first protruding column, and the second channel is disposed in the second protruding column; the at least one soft plug is airtightly fixed to an end of the first protruding column and an end of the second protruding column, which are away from the barrel.

12. The closed system transfer device as claimed in claim 11, wherein the at least one soft plug comprises a first soft plug and a second soft plug; the first soft plug is airtightly fixed to an end of the first protruding column, which is away from the barrel; the second soft plug is airtightly fixed to an end of the second protruding column, which is away from the barrel.

13. The closed system transfer device as claimed in claim 11, wherein the first protruding column and the second protruding column are fixed to the second end opening of the second tube body of the barrel; the first channel in the first protruding column corresponds to and communicates with the first cavity of the barrel; the connecting port comprises at least one sleeve body for receiving the first protruding column and the second protruding column; the at least one soft plug is airtightly clamped between the first protruding column, the second protruding column, and the at least one sleeve body; the at least one sleeve body has a first wall and a second wall, which face opposite directions; the first protruding column corresponds to the first wall of the at least one sleeve body, and the second protruding column corresponds to the second wall of the at least one sleeve body.

14. The closed system transfer device as claimed in claim 13, wherein the at least one sleeve body comprises a first sleeve body and a second sleeve body; the at least one soft plug comprises a first soft plug and a second soft plug; the first sleeve body is adapted to receive the first protruding column, and the second sleeve body is adapted to receive the second protruding column; the first soft plug is airtightly clamped between the first protruding column and the first sleeve body; the second soft plug is airtightly clamped between the second protruding column and the second sleeve body.

15. The closed system transfer device as claimed in claim 1, comprising a hub that is detachably connected to the connecting port, wherein the hub comprises a first end portion and a second end portion, which are opposite to each other; the first end portion comprises a first needle and a second needle, wherein the first needle and the second needle extend in the same direction and are adjacent to each other; when the first end portion of the hub is connected to the connecting port, the first needle and the second needle are inserted through the at least one soft plug to allow the first needle to be inserted into the first channel, and the second needle to be inserted into the second channel; the second end portion of the hub is detachably connected to the drug liquid container and communicates with the first needle of the first end portion.

16. The closed system transfer device as claimed in claim 15, wherein the first end portion comprises a hollowed column and an elastic member; the first needle, the second needle, and the elastic member are located in the hollowed column; when the hub does not be connected to the connecting port, the elastic member covers the first needle and the second needle.

17. The closed system transfer device as claimed in claim 16, wherein a longitudinal direction of the hollowed column is parallel to a longitudinal direction of the first needle and the second needle; when the hub is connected to the connecting port, the elastic member is operably pressed along the longitudinal direction of the hollowed column toward the second end portion to allow the first needle and the second needle to protrude out of the elastic member and insert through the at least one soft plug.

18. The closed system transfer device as claimed in claim 16, wherein the elastic member comprises an external elastomer and an internal elastomer; the external elastomer covers the internal elastomer, and the external elastomer is located between the hollowed column and the internal elastomer; when the hub does not be connected to the connecting port, the internal elastomer surrounds the first needle and the second needle, and the external elastomer covers the first needle and the second needle; when the hub is connected to the connecting port, the external elastomer and the internal elastomer is pressed by the connecting port to move along a longitudinal direction of the hollowed column toward the second end portion, so that the first needle and the second needle protrude out of the external elastomer and insert through the at least one soft plug.

19. The closed system transfer device as claimed in claim 18, wherein when the hub is disengaged from the connecting port, the external elastomer and the internal elastomer rebound along the longitudinal direction of the hollowed column away from the second end portion; during the disengagement process of the hub, the internal elastomer urges the external elastomer to continuously contact with the connecting port until the first needle and the second needle is covered by the external elastomer again.

20. The closed system transfer device as claimed in claim 16, wherein the connecting port comprises an annular wall; the annular wall is adapted to correspondingly fit around the hollowed column; an inner circumference of the annular wall comprises a slot, and an outer circumference of the hollowed column comprises a rib; when the annular wall correspondingly fits around the hollowed column, the slot is engaged with the rib to guide the first needle and the second needle to correspondingly insert into the first channel and second channel, respectively.

21. The closed system transfer device as claimed in claim 15, wherein the second end portion comprises a lancet; the lancet could be detachably connected to the drug liquid container; the lancet comprises a first pathway and a second pathway, wherein the first pathway and the second pathway are separated from each other; the first pathway communicates with the first needle, and the second pathway communicates with the second needle.

22. The closed system transfer device as claimed in claim 21, wherein an opening of the first pathway of the lancet is greater than an opening of the second pathway of the lancet.

23. The closed system transfer device as claimed in claim 15, wherein the second end portion comprises an infusion needle and a ferrule, the infusion needle comprises a pathway, the pathway communicates with the first needle; the ferrule comprises an internal thread is adapted to be detachably screwed with an external thread of the drug liquid container; the hub comprises an anti-reverse flow pad, which is located between the second end portion and the second needle, thereby isolating the pathway from the second needle.

24. The closed system transfer device as claimed in claim 1, wherein the connecting port comprises the first channel, the second channel, an elastic member, an anti-leakage ring, and the at least one soft plug; the first channel communicates with the first cavity, and the second channel communicates with the second cavity; the anti-leakage ring is airtightly fixed to an end of the first channel and an end of the second channel.

25. The closed system transfer device as claimed in claim 24, comprising a hub detachably connected to the connecting port, wherein the hub comprises a first end portion and a second end portion; a first needle and a second needle, wherein the first needle and the second needle extend in the same direction and are adjacent to each other; the at least one soft plug comprises a first soft plug and a second soft plug; when the first end portion of the hub is connected to the connecting port, a top concave of the first needle urges against the first soft plug, and a top concave of the second needle urges against the second soft plug, so that the first needle correspondingly communicates with the first channel, and the second needle correspondingly communicates with the second channel; the second end portion of the hub is detachably connected to the drug liquid container, and the second end portion of the hub communicates with the first needle of the first end portion.

26. The closed system transfer device as claimed in claim 25, wherein when the first end portion of the hub is connected to the connecting port, the top concave of the first needle urges the first soft plug, and the top concave of the second needle urges the second soft plug; the first and second soft plugs urge the elastic member to press the elastic member in a direction toward the second end opening of the barrel.

* * * * *